United States Patent
Gunn

(10) Patent No.: US 8,468,033 B2
(45) Date of Patent: Jun. 18, 2013

(54) CLOUD-BASED HEALTHCARE INFORMATION EXCHANGE

(75) Inventor: Shane W. Gunn, Danvers, MA (US)

(73) Assignee: CareXGen, Inc., Medina, TN (US)

( * ) Notice: Subject to any disclaimer, the term of this patent is extended or adjusted under 35 U.S.C. 154(b) by 151 days.

(21) Appl. No.: 12/840,969

(22) Filed: Jul. 21, 2010

(65) Prior Publication Data

US 2011/0119088 A1    May 19, 2011

Related U.S. Application Data

(60) Provisional application No. 61/227,314, filed on Jul. 21, 2009.

(51) Int. Cl.
*G06Q 10/00* (2012.01)
*G06Q 50/00* (2012.01)

(52) U.S. Cl.
USPC .................................. 705/2; 705/3; 370/351

(58) Field of Classification Search
USPC .......................................... 705/2–3; 370/351
See application file for complete search history.

(56) References Cited

U.S. PATENT DOCUMENTS

| | | | |
|---|---|---|---|
| 2004/0059598 A1 | 3/2004 | Wellons et al. | |
| 2007/0030066 A1 | 2/2007 | Sohn et al. | |
| 2009/0080408 A1* | 3/2009 | Natoli et al. | 370/351 |
| 2009/0307755 A1* | 12/2009 | Dvorak et al. | 726/4 |
| 2010/0145728 A1* | 6/2010 | Azancot | 705/3 |

FOREIGN PATENT DOCUMENTS

| | | |
|---|---|---|
| EP | 1 122 652 A1 | 8/2001 |
| WO | WO-98/13783 A1 | 4/1998 |

* cited by examiner

*Primary Examiner* — Luke Gilligan
(74) *Attorney, Agent, or Firm* — Foley & Lardner LLP; Christopher J. McKenna

(57) ABSTRACT

The present disclosure describes systems and methods of a healthcare exchange system to exchange medical information, stored in different formats, between different entities. This exchange system provides a channel for the flow of information and patient records across different health care entities that may store data in different formats. The exchange system's ability to receive requests and retrieve corresponding data from various entities, along with the transformation of data from the storing format into a format specified by the requesting entity, allow a flexible and extendable healthcare information exchange system.

20 Claims, 8 Drawing Sheets

CLOUD-BASED HEALTHCARE INFORMATION EXCHANGE

RELATED APPLICATION(S)

This application claims priority and the benefit of U.S. Provisional Application No. 61/227,314, filed Jul. 21, 2009 and entitled "Cloud-based Healthcare Information Exchange", which is incorporated herein by reference in its entirety.

BACKGROUND

Many efforts have been made to solve the Healthcare IT industry problems that hide within the walls of most hospitals, PHO's, IPA's and practices. Typically though, issues are exacerbated by all the vendors who build a proprietary client server solution to fix one problem within one organization and then try to apply that solution across the healthcare IT industry as a utopian solution with the expectation that everyone will utilize their solution without any way for the data, the application or device collected data to be passed to the next application that sits on a server two feet from it on the same network. This type of solution is the most costly in every way possible. The cost of ownership when you break down the benefits versus revenue is never justified. This creates an unlevel playing field for healthcare organizations versus healthcare technology vendors.

The healthcare organizations typically do not have the skill sets in-house to design IT solutions beyond the healthcare organization's needs of that moment. This makes it very easy to purchase healthcare software and devices that will not communicate without yet another piece of software, servers and skill sets that are few and far between. Building interfaces so all software can communicate with each other has fallen into the same place as the utopian software solutions. (Example: We just need lab system results to connect to this electronic medical record.)

SUMMARY OF THE INVENTION

The present solution provides systems and methods for a healthcare information exchange that addresses the above mentioned issues as well as other issues. The solution provides a peer to peer health information data exchange that interfaces or communicates with any electronic medical records systems.

The present solution offers a health information exchange that does not require the normal 'repository' model. The present solution uses a peer to peer model that avoids the creation of large data silos that are expensive to build and maintain. The healthcare information exchange system will allow for improvement in the quality of care of patients, improvement in the reporting of illnesses and other quality initiatives and lower the overall cost of healthcare.

In the present solution, data is stored with the originating creator of the patient record (the practice, the IPA, PHO, hospital, etc.) and is shared when needed by another physician. This effectively manages the consent process since creators of the patient record will ensure that proper consent of their patients is obtained at the point in time the record is required by another or prior to being shared. This is similar to the HIPAA statements all patients are required to sign when going to the doctor's office.

The healthcare exchange system uses a peer to peer method of 'sharing' patient data, which is similar to what popular viral sites such as iTunes, Twitter, or Facebook use today. This approach replicates quickly, efficiently, and can easily become the 'standard' by which healthcare data is shared:

The present solution avoids the issues and costs of technologies that exist today in healthcare organizations, which include but are not limited to: License/Device Cost, Maintenance, Hardware, Support and Maintenance. Current technologies may further require implementation costs and time for tasks such as System Training, Continued Training, New Employee Training, Integration, Software Licenses and Maintenance for software and implementation.

BRIEF SUMMARY OF THE INVENTION

The present disclosure describes systems and methods of a healthcare exchange system to exchange medical information, stored in different formats, between different entities. This exchange system provides a channel for the flow of information and patient records across different health care entities that may store data in different formats. The exchange system's ability to receive requests and retrieve corresponding data from various entities, along with the transformation of data from the storing format into a format specified by the requesting entity, allow a flexible and extendable healthcare information exchange system.

In one aspect, the present invention relates to a method for exchanging healthcare information via a healthcare exchange system. The method comprises receiving, by a healthcare exchange system in communication with a plurality of health care entities via one or more networks a first request, from a first application of a first healthcare entity, for medical information of a patient or a plurality of patients. The method further includes identifying, by the healthcare exchange system, that a second healthcare entity has a medical record or a plurality of medical records of the patient. The medical record may be stored by the second healthcare entity in a second format identified by a second profile of the second healthcare entity. The healthcare exchange system may transmit, via one or more networks, a second request to the second healthcare entity for release of the medical record. In one embodiment, the healthcare exchange system may receive, via one or more networks, the medical record of the patient in the first format responsive to release of the medical record by the second healthcare entity. In another embodiment, the healthcare exchange system may automatically transform the medical record to a first format identified by a first profile of the first healthcare entity. In some aspect, responsive to the first request, the healthcare exchange system may transmit, via one or more networks, the medical record in the second format to the first healthcare entity responsive to the first request.

In some embodiments, the healthcare exchange system may receive the first request comprising a query for information on the patient accessible via the healthcare exchange system. The healthcare exchange system may also receive the first request comprising a query for a specific type of medical record of the patient. In another embodiment, the healthcare exchange system may query patient information stored by the healthcare exchange system, which may store portions of patient records transmitted between entities via the healthcare exchange system. The healthcare exchange system may further store a healthcare exchange record for the patient that identifies a healthcare entity and an application from which one or more medical records of the patient is stored externally from the healthcare exchange system.

In another embodiment, the healthcare exchange system may transmit, via one or more networks, the second request to the second healthcare entity for release of the medical record via an interface compatible with a second application of the second healthcare entity. In one embodiment, the healthcare exchange system may receive, via one or more networks, the medical record of the patient in the second format from a second application of the second healthcare entity. In some embodiment, the healthcare exchange system may receive, via one or more networks, the medical record of the patient via a message type identified by the second profile of the second healthcare entity. In an embodiment, the healthcare exchange system may identify the first profile of the first healthcare entity stored in the healthcare exchange system, and the first profile may identify the first healthcare entity and format version of a sending application. In another embodiment, the healthcare exchange system may transmit, via one or more networks, the medical record via a message type identified by the first profile of the first healthcare entity.

In one aspect, the present invention relates to a system for exchanging healthcare information via a healthcare exchange system. The system comprises a healthcare exchange system operating on one or more servers and in communication with a plurality of health care entities via one or more networks. The healthcare exchange system may receive a first request, from a first application of a first healthcare entity, for medical information of a patient of a plurality patients. The system may further include a database of the healthcare exchange system identifying that a second healthcare entity has a medical record or a plurality of medical records of the patient. The medical record may be stored by the second healthcare entity in a second format identified by a second profile of the second healthcare entity. The healthcare exchange system, via one or more networks, may transmit a second request to the second healthcare entity for release of the medical record and receive the medical record of the patient in the first format responsive to release of the medical record by the second healthcare entity. In some embodiment, the system may also include an engine of the healthcare exchange system transforming the medical record to a first format identified by a first profile of the first healthcare entity. The healthcare exchange system may transmit, via one or more networks, the medical record in the second format to the first healthcare entity responsive to the first request.

In some embodiments, the healthcare exchange system may receive the first request comprising a query for information on the patient accessible via the healthcare exchange system. In another embodiment, the healthcare exchange system may receive the first request comprising a query for a specific type of medical record of the patient. In an embodiment, the healthcare exchange system may query patient information stored by the healthcare exchange system, which may store portions of patient records transmitted between entities via the healthcare exchange system. In some aspect, the database in the system may store a healthcare exchange record for the patient that identifies a healthcare entity and an application from which one or more medical records of the patient is stored externally from the healthcare exchange system.

In another embodiment, the healthcare exchange system may transmit, via one or more networks, the second request to the second healthcare entity for release of the medical record via an interface compatible with a second application of the second healthcare entity. In some other embodiment, the healthcare exchange system may also receive, via the one or more networks, the medical record of the patient in the second format from a second application of the second healthcare entity.

In one embodiment, the healthcare exchange system may receive, via one or more networks, the medical record of the patient via a message type identified by the second profile of the second healthcare entity. In some embodiment, the healthcare exchange system may identify the first profile of the first healthcare entity stored in the healthcare exchange system, and the first profile may identify the first healthcare entity and format version of a sending application. In another embodiment, the healthcare exchange system may transmit, via one or more networks, the medical record via a message type identified by the first profile of the first healthcare entity.

The details of various embodiments of the invention are set forth in the accompanying drawings and the description below.

BRIEF DESCRIPTION OF THE FIGURES

The foregoing and other objects, aspects, features, and advantages of the invention will become more apparent and better understood by referring to the following description taken in conjunction with the accompanying drawings, in which.

Figure 1A:
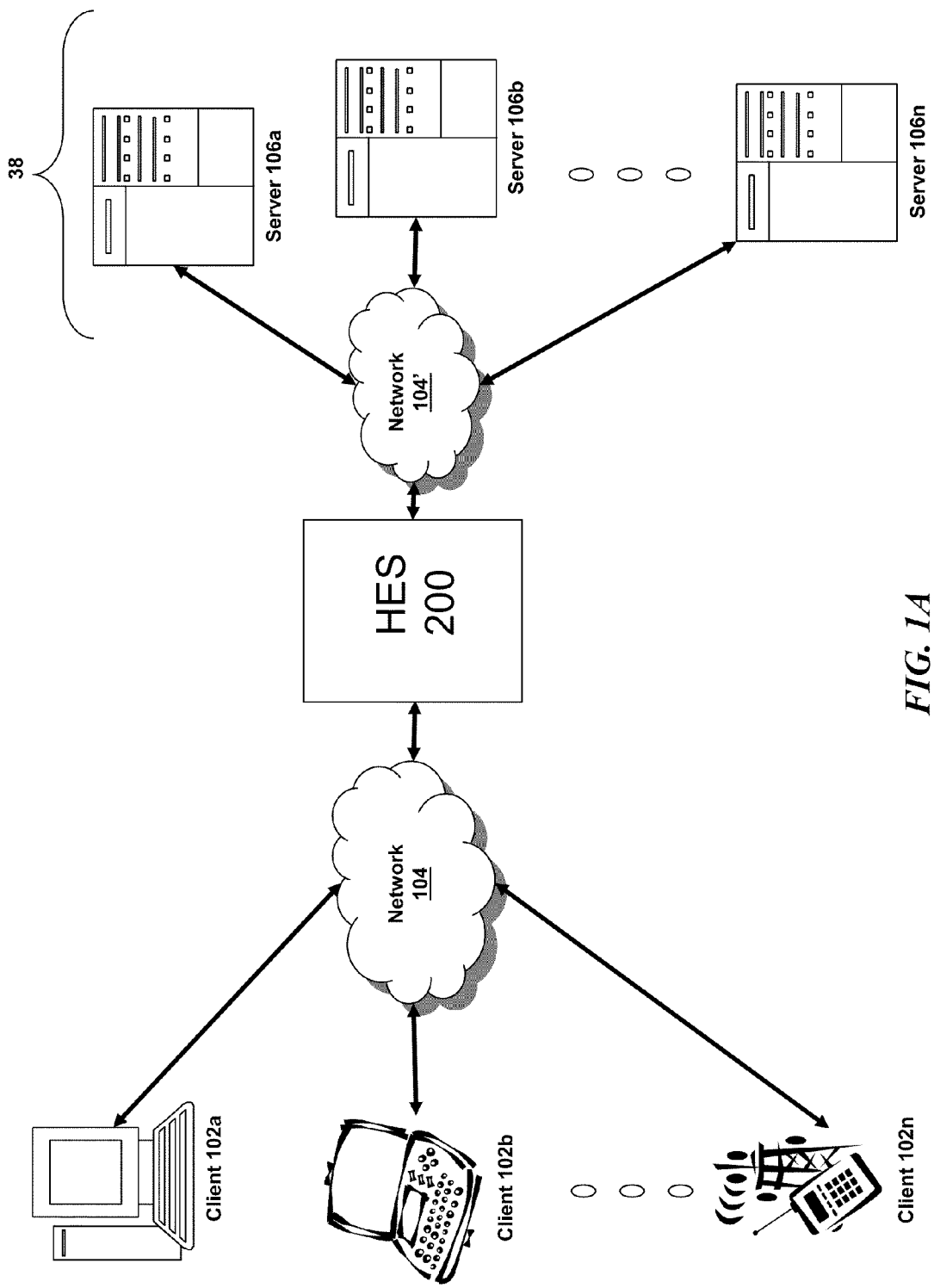
FIG. 1A is a block diagram of an embodiment of a network environment for a healthcare exchange system.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Prior to discussing the specifics of embodiments of the systems and methods of the healthcare exchange system, it may be helpful to discuss the network and computing environments in which such embodiments may be deployed. Referring now to FIG. 1A, an embodiment of a network environment is depicted. In brief overview, the network environment comprises one or more clients 102a-102n (also generally referred to as local machine(s) 102, or client(s) 102) in communication with one or more servers 106a-106n (also generally referred to as server(s) 106, or remote machine(s) 106) via one or more networks 104, 104' (generally referred to as network 104). In some embodiments, a client 102 and/or a server 106 communicate via a healthcare exchange system, referred to as HES 200. In some embodiments, the HES may be deployed or accessed via any type and/or form of cloud services or systems to provide a cloud-based healthcare information exchange.

Although FIG. 1A shows a network 104 and a network 104' between the clients 102 and the servers 106, the clients 102 and the servers 106 may be on the same network 104. The networks 104 and 104' can be the same type of network or different types of networks. The network 104 and/or the network 104' can be a local-area network (LAN), such as a company Intranet, a metropolitan area network (MAN), or a wide area network (WAN), such as the Internet or the World Wide Web. In one embodiment, network 104' may be a private network and network 104 may be a public network. In some embodiments, network 104 may be a private network and network 104' a public network. In another embodiment, networks 104 and 104' may both be private networks.

The network 104 and/or 104' may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, a SDH (Synchronous Digital Hierarchy) network, a wireless network and a wireline network. In some embodiments, the network 104 may comprise a wireless link, such as an infrared channel or satellite band. The topology of the network 104 and/or 104' may be a bus, star, or ring network topology. The network 104 and/or 104' and network topology may be of any such network or network topology as known to those ordinarily skilled in the art capable of supporting the operations described herein.

As shown in FIG. 1A, the HES 200 is shown between the networks 104 and 104'. In some embodiments, the HES 200 may be located on network 104. In other embodiments, the HES 200 may be located on network 104'. In yet another embodiment, a plurality of HES 200 may be deployed on network 104. An HES 200 may be located at any point in the network or network communications path between a client 102 and a server 106. In yet another embodiment, HES may be deployed on a third network, and devices such as clients and servers communicate via network 104 or 104' to access the services of the HES. For example, the HES may be deployed on a hosted service provider, such as a cloud service provider, and client and servers via a public or private network access the HES, executing on servers of the cloud service provider.

An information technology infrastructure may extend from a first network—such as a network owned and managed by an enterprise—into a second network, which may be owned or managed by an entity separate from the entity owning or managing the first network. Resources provided by the second network may be said to be "in a cloud". Cloud-resident elements may include, without limitation, storage devices, servers, databases and applications. In various embodiments, one or more networks providing computing infrastructure on behalf of customers may be referred to as a cloud. In one of these embodiments, a system in which users of a first network access at least a second network including a pool of abstracted, scalable, and managed computing resources capable of hosting user resources may be referred to as a cloud computing environment. In another of these embodiments, resources may include, without limitation, data center resources, applications, and management tools. In some embodiments, Internet-based applications (which may be provided via a "software-as-a-service" or "platform-as a service" model) may be referred to as cloud-based resources.

The HES, sometimes referred to as Dynamic Naming Attribute (DNA) system, may comprise any combination of hardware and software. The HES may comprise an application, program, library, script, process, service, task or any other type and form of executable instructions. The HES may be modular and may be made up of a plurality of components. Each component may comprise executable instructions directed to a set of functionality, logic or operations. The HES may be distributed and deployed and executed on one or more servers. The HES may be distributed and deployed and executed on one or more clients and servers. The HES may comprise any type and form of web service. The HES may comprise any type and form of web-based or Internet application. The HES may comprise any type and form of SaaS or PaaS. The HES may be deployed as an enterprise type application with software installed on one or more devices of an enterprise.

The HES may comprise any logic, business rules, function and operations to provide an exchange information system, such as in some embodiments, a healthcare exchange information system. The HES may provide a flexible, configurable and efficient system for the identification, transformation and exchange of various information, data and documents between disparate systems and formats. End users of the HES can request, transmit and/or exchange documents, such as patient and medical records, without understanding the underlying technologies necessary to interface, communicate, transform and exchange such information. These end users can work with their native applications and formats and seamlessly and transparently receive documents from different applications and formats from other users.

The HES and any applications of entities or end users may operate on a plurality of servers. In one embodiment, the system may include multiple, logically-grouped servers 106. In these embodiments, the logical group of servers may be referred to as a server farm 38. In some of these embodiments, the serves 106 may be geographically dispersed. In some cases, a farm 38 may be administered as a single entity. In other embodiments, the server farm 38 comprises a plurality of server farms 38. In one embodiment, the server farm executes one or more applications on behalf of one or more clients 102.

The servers 106 within each farm 38 can be heterogeneous. One or more of the servers 106 can operate according to one type of operating system platform (e.g., WINDOWS NT, manufactured by Microsoft Corp. of Redmond, Wash.), while one or more of the other servers 106 can operate according to another type of operating system platform (e.g., Unix or Linux). The servers 106 of each farm 38 do not need to be physically proximate to another server 106 in the same farm 38. Thus, the group of servers 106 logically grouped as a farm 38 may be interconnected using a wide-area network (WAN) connection or medium-area network (MAN) connection. For example, a farm 38 may include servers 106 physically located in different continents or different regions of a continent, country, state, city, campus, or room.

Servers 106 may be referred to as a file server, application server, web server, proxy server, or gateway server. In some embodiments, a server 106 may have the capacity to function as either an application server or as a master application server. In one embodiment, a server 106 may include an Active Directory. The clients 102 may also be referred to as client nodes or endpoints. In some embodiments, a client 102 has the capacity to function as both a client node seeking access to applications on a server and as an application server providing access to hosted applications for other clients 102a-102n.

Figure 1B:
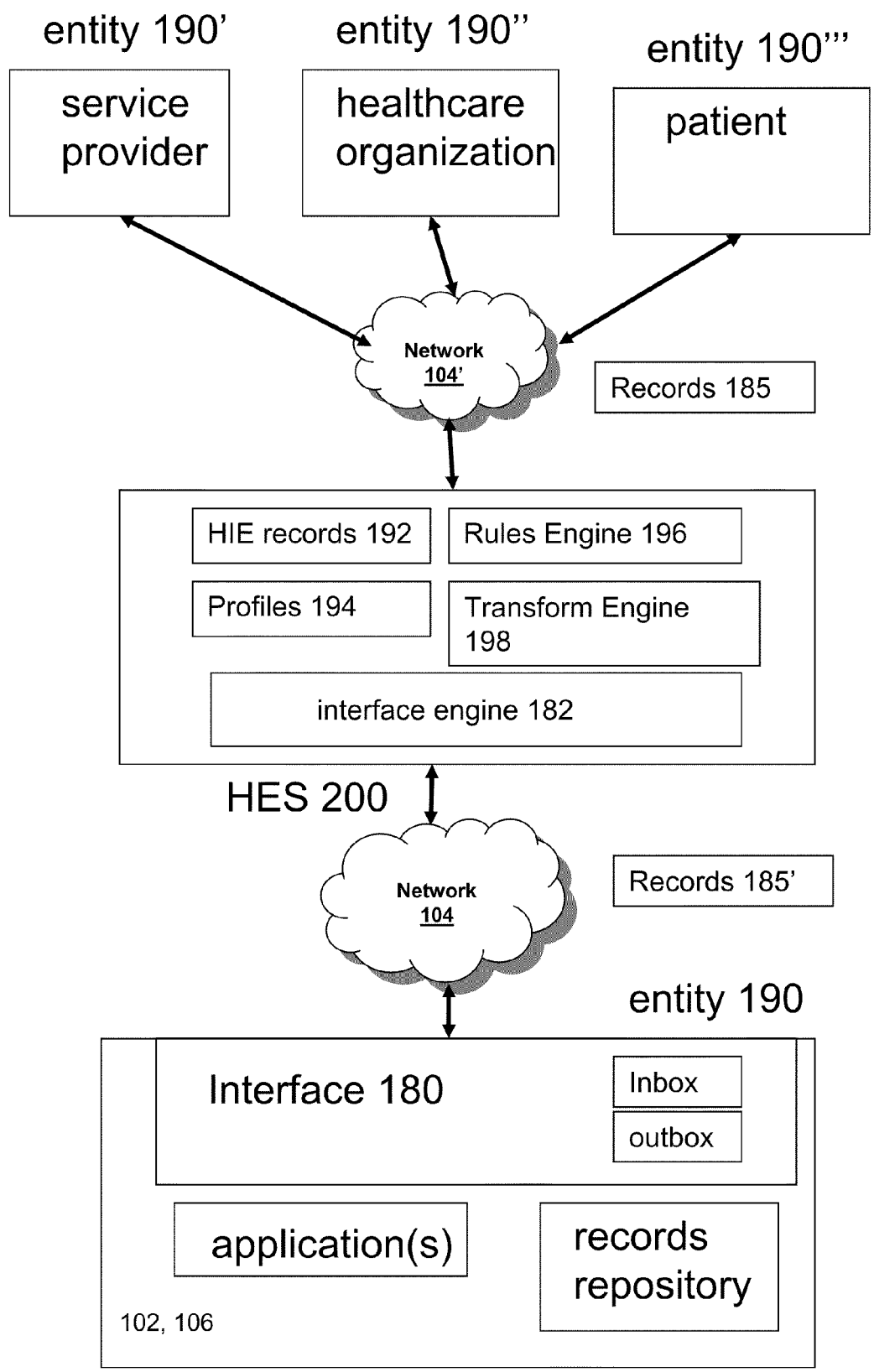
FIG. 1B is a block diagram of another embodiment of an environment for a healthcare exchange system.

Referring now to FIG. 1B, an embodiment of a healthcare environment deploying the HES 200 is depicted. A plurality of entities 190-190''' may be in communication with the HES 200 via one or more networks 104, 104'. The entities may include healthcare related service providers 190', healthcare organizations 190'' and/or patients 190'''. A device, such as a client or server, of the entity may include one or more applications, an interface 180 to the HES and data repository storing any healthcare related records. Via an inbox and outbox of the interface 180, the entity may exchange data and information, such as records 185, 185' from the application(s) and/or records repository. The HES may have an interface engine to interface with different types and forms of interfaces 180 of entities. The HES may store HIE records 192 to identify patients and the storage of patient medical records externally at any entity 190-190''', such as in the records repository or application of entity 190. The HES may include profiles 194, such as entity profiles, application profiles and message profiles to perform any of the operations and functionality of the HES. The HES may include a rule engine that determines rules for exchanging and transforming information via the exchange. The HES may also include a transform or transformation engine 198 for transforming data from one format to another format.

The entity 190-190''', generally referred to as 190, may include or be any type and form of entity. The entity may be a person such as a patient or doctor. The entity may be a service provider, such as any company, organization or group of people who perform one or more services. In the healthcare context, a service provider may be any doctor's office, doctor's practice, clinic, hospital, lab, pharmacy or any other healthcare related provider of services. In some embodiments, the entity may be any type and form of healthcare organization including insurance companies, medical and research organizations and the like.

An entity may execute, operate or otherwise provide an application, which can be any type and/or form of software, program, or executable instructions such as any type and/or form of web browser, web-based client, client-server application, a thin-client computing client, an ActiveX control, or a Java applet, or any other type and/or form of executable instructions capable of executing on a device 100, such as a client or server.

In some embodiments, an application may provide any type and form of healthcare related application or information system. In some embodiments, the application may be a patient registration application. In some embodiments, the application may be an insurance administrative application. In some embodiments, the application may be a healthcare billing system. In some embodiments, the application may be a medical records related application. In some embodiments, the application may be a healthcare practice related application.

The application may store one or more records into a records repository, which may be any type and form of database or file system. The application may store and process records in a format understood by the application. The application may store and process records in a format native to the application. The application may process records in one format and store the records in another format. The application may export records from the application or repository into another format, which may be selectable by a user.

In embodiments of a healthcare related environment, the application may process any type and form of patient records and store such records into the records repository. The application may process any type and form of medical record of a patient and store the medical record into the records repository. The application may process any type and form of medical history information of a patient and store such information into the records repository. In any of these embodiments, the records repository may contain data and information that can be arranged to form a copy of a patient's record or one or more medical records. Such data and information may include doctor's notes, test or lab results and any other written or electronic information associated with the care of a person.

Each of the entities may have disparate and different applications than other entities. A first entity may store in a first records repository a first medical record of a patient processed or produced by a first application using a first format. A second entity may store in a second records repository a second medical record of a patient processed or produced by a second application using a second format. A plurality of applications and records repositories located at a plurality of different entities may each include different records of the same patient. A plurality of applications and records repositories located at a plurality of different entities may each include some of the same records of the same patient. A plurality of applications and records repositories located at a plurality of different entities may each include a combination of the same and different records of the same patient. As such, in some embodiments, the records of any patient may be distributed disparately across a plurality of entities, applications and/or repositories in different formats.

Furthermore, any applications may communicate using any type and form of communication protocols, such as any type and form of healthcare or medical related data formats and protocols. In some embodiments, the first entity storing a first record in a first format may communicate using a first message type or communications protocol while a second entity storing a second record in a second format may communicate using a second message type or communications protocol. As such, in some embodiments, the records of any patient may have to be communicated between entities that support or use different data formats and/or communication protocols.

The entity may execute, deploy or implement any type and form of interface 180 to the HES. In some embodiments, the interface 180 implements an inbox for receiving data, information and messages from the HES and an outbox for transmitting data, information and messages to the HES. In some embodiments, the interface may be any type and form of executable instructions, including an application, program, script or library. The interface may use any type and form of TCP/IP communications to communicate with the HES, such as any type of sockets based communications. The interface may use any type and form of folders or directory structure to implement the inbox and outbox. The interface may run in the background in some embodiments. The interface may be installed seamlessly and transparently to the user. The interface may be transmitted from the HES to a device of the entity and automatically executed on the device, such as without any installation or interaction by the user.

In some embodiments, the interface may include any type and form of user interface: graphical, command or otherwise. The interface may be a web based user interface to receive input from a user to submit data, information or messages to the HES and/or receive data, information or messages from the HES. For example, the interface may comprise a web page for a user to select a name of a patient and query patient information from the HES. The interface may include executable instructions to send, receive and view documents via the HES. In some embodiments, the interface may be integrated with, included in or constructed in any of the applications. The interface may include any database interfaces or drivers to access any records repository or application database. The interface may include any application programming interfaces or libraries for accessing any records repository or application database. The interface may include any application programming interfaces for interfacing or communicating with any application.

The HES may include an interface engine 182. The interface engine may include any type and form of executable instructions executable or executing on a device. The interface engine may comprise an interface corresponding to the interface 180 of an entity. The interface engine may comprise any of the types of interfaces described in connection with interface 180. The interface engine may support and implement a plurality of different types of interfaces. For example, each of the entities 190-190''' may have a different type of interface to the HES but a single interface engine 180 handles and processes communications with each entity's interface.

The interface and/or interface engine may support, implement and communicate using any portion or version of the HL7 Clinical Document Architecture (CDA), which is an XML based markup standard intended to specify the encoding, structure and semantics of clinical documents for exchange. CDA is part of the HL7 version 3 standard. Akin to other parts of the HL7 version 3 standard, it was developed using the HL7 development Framework (HDF) and it is based on the HL7 Reference Information Model (RIM) and the HL7 Version 3 Data Types. CDA documents are persistent in nature. The CDA specifies that the content of the document consists of a mandatory textual part (which ensures human interpretation of the document contents) and optional structured parts (for software processing). The structured part relies on coding systems (such as from SNOMED and LOINC) to represent concepts. The CDA standard doesn't specify how the documents should be transported. CDA documents can be transported using HL7 version 2 messages, HL7 version 3 messages, as well as by other mechanisms, such as DICOM, MIME attachments to email, http or ftp. In the U.S., the CDA standard is probably best known as the basis for the Continuity of Care Document (CCD) specification, based on the data model as specified by ASTMs Continuity of Care Record. The U.S. Healthcare Information Technology Standards Panel has selected the CCD as one of its standards. See also HL7 EHRcom Health Informatics Service Architecture (HISA).

The interface and/or interface engine may comprise any version of Java Web Start, which allows users to start software from the network or Internet using a browser. In some embodiments, the HES and/or interface engine provides the interface to the entity. For example, a user at an entity may login to or access the HES via a web page. The interface engine may automatically provide and start the interface or portions thereof on the device of the entity. In some embodiments, the browser at the entity may automatically install and/or execute the interface.

The interface and/or interface engine may comprise any type and form of file transfer technology, implementations or programs. The interface and/or interface engine may comprise any type and form of secure file transfer. The interface and/or interface engine may comprise any version of HyperSend, which provide secure internet delivery solutions.

The interface may comprise any peer-to-peer technology for sending and receiving files between devices of entities. The interface may include any technology from BitTorrent to provide peer-to-peer interfaces and communications. The interface may implement any peer-to-peer data or file sharing protocols. In some embodiments, HyperSend provides a peer to peer interface between devices. In some embodiments, the peer-to-peer communications are between a device of one entity and a device of another entity. In some embodiments, the peer-to-peer communications traverse one or more devices of the HES. In some embodiments, the HES establishes and/or facilitates the peer-to-peer communications between entities.

The interface may include any type of file or explorer interface to view, access and exchange files or documents in the inbox and outbox of the entity running the interface and the inbox and/or outbox of another entity. From a device of one entity, a user may be able to view the inbox and outbox via interface of the entity and request files to share, move, view, etc. For example, the user may be able to drag and drop a file from the entity's outbox to another entity's inbox.

The HES and/or interface engine may provide, download, install and/or execute the interface on, for or on behalf of the entity. The interface may be provided, installed and/or executed responsive to any type of access via the HES, such as upon login or transmitting a request. The interface may be provided, installed and/or executed upon demand or request from a user.

The interface may be installed using any type and form of installer or installation process. In some embodiments, the interface is installed using a silent install process running in the background that does not require any user interaction to complete. In some embodiments, the interface is transparently executed and running in the background and does not require any user interaction.

In some embodiments, the HES uses any type and form of clientless install or virtualized installation to provide the interface to an entity. In some embodiments, the HES uses any version of InstallFree application virtualization technology from InstallFree, Inc. For example, in some embodiments, InstallFree software may be stored on a folder on the network accessible to active directory, such as the following.

---

C:\InstallFree_Software
C:\InstallFree_Software\Applications
    Hypersend
C:\InstallFree_Software\Users
    Security Group/Organization Unit (Login Script to deliver the InstallFree Bridge to the Application Directory and Installfree User Profiles)
        Registration
            Usernames included in the group

---

Once the user logs into the Windows workstation or terminal server, the interface appears installed to the user with all the functionality of an installed application. If this user works at more than one location, the same login script follows the user to every workstation delivering that interface application even if the workstation's operating system has changed. For instance, if the first windows workstation is running Windows XP service pack 2 and the next workstation is running Vista service pack 1, the interface runs the same for the user.

This type of approach can be viewed from a Healthcare Data Exchange point of view. Placing the Healthcare Data Exchange Software (DNA) in the Cloud and delivering the InstallFree Bridge over HTTPS or Secure Socket Layer means it is possible, from a web address with which every desktop or server with internet can communicate, to manage which registered user gets the interface without the install of the interface, regardless of their operating system.

The HES may generate, process and store records referred to as HIE records. The HES may identify any data and information regarding a patient from any transmission or exchange of data traversing the HES. For example, the HES may identify patient information from unstructured data in Word documents, PDFs, faxes and the like that traverse the HES. The HES may identify and form structure to such unstructured data and store the data in a database or repository 192 of the HES. The HES may convert various non-structured data, which comprise patient records, to structured data such as in the HL7 standard. The HES may have a loading or upload or other function that allows an entity to transmit or provide a plurality of records of a plurality of patients to the HES for creating or pre-populating HIE records. The HES may store the HIE records in one or more databases of the HES. These databases may be deployed in a cloud storage system.

The HIE records 192 in one aspect provide a "global positioning system" for patient records stored externally to the HES system across a plurality of disparate entities, applications and systems. The HES identifies patient information and stores in structured records 192 information identifying the entities and applications providing or storing patient records. In this manner, the HES does not store copies of all the records of a patient but instead stores meta data and other identifying information that identifies a patient and pointers to external entities and applications to obtain the records of the patient. In this approach, a patient's medical records may be stored as they are naturally are at any entity and another entity may obtain such medical records on demand or as requested.

The HES may include one or more profiles 194. The profile may comprise any object, data structure or database data. A profile may be associated with or configured for an entity, an application or a message. A profile may identify one or more characteristics or attributes of the entity, application or message. A profile may be unique to each entity, application or message. The HES may create or generate a profile for an entity upon registration of the entity with the HES. The HES may create or generate a profile for an application based on input from the entity about the application. The HES may create or generate a profile for a message based on communications via the HES. The HES may use any of these profiles in the operations and methods of the HES.

An entity profile, which may be referred to as an organization or provider profile, may include any bibliographic or contact information identifying the entity. The entity profile may include any National Provider Identifier (NPI), such as any via the NPI Plan and Provider Enumeration System. The entity profile may include any tax identifier. The entity profile may include any employer or corporate identifier. The entity profile may include any certified system identifier. The entity profile may include any identifier generated by the HES and assigned to the entity. The entity profile may include identifiers of any entity applications or pointers/identifiers to any application profiles. In some embodiments, the entity profile may include one or more application profiles.

An application profile may include any name or identifier of the application. The application profile may identify or specify any file formats supported or used by the application. The application profile may identify or specify any data formats supported or used by the application. The application profile may identify or specify any protocols supported or used by the application. The application profile may identify or specify any versions of file and data formats and/or protocols supported or used by the application. The application profile may identify or specify any HL7 versions and specs accepted. The application profile may identify or specify any XML standards. The application profile may identify or specify any custom or proprietary formats. The application profile may identify or specify any national clinical data backbone. The application profile may identify or specify any names and/or codes of the Logical Observation Identifiers Names and Codes (LOINC of loinc.org). The application profile may identify or specify any names and/or codes of SNOMED (Systemized Nomenclature of Medicine-Clinical Terms). The application profile may identify or specify any custom names and/or codes. The application profile may include any certified system identifier. The application profile may include any identifier generated by the HES and assigned to the application.

The message profile comprises a profile identifying attributes of an instance of a message communicated via the exchange, such as a request message from one entity for a record of a patient stored at another entity. The message profile may be created by the HES via message headers and formats. Messages to and/or from the HES may comprise a predetermined format. In some embodiments, the message may include via the header and/or body, any of the following elements:

Sending Location (e.g. Labs);
Receiving Location (e.g. Medical Practice);
Message Type (e.g. ORU, MDM);
Format Version of Application (e.g. HL7 2.3); and/or
ACK Message Requirements for sending systems.

The sending and receiving locations may be identified via entity profiles, such as via identifiers of entity profiles. In some embodiments, the sending and receiving locations may be identified via system identifiers or HES provided identifiers. In some embodiments, the sending and receiving locations may be identified by entity names, such as names stored in the entity profile. The message type may include the type of message being sent. The message type may include the type of message being carried by the body of the message. In some embodiments, the message type identifies a type of message under any clinical or medical protocol. In some embodiments, the message type identifies a type of message generated or used by any application, such as any healthcare related application. The format version may identify the format and version of the data or protocol used by the application to generate or provide the data. The message profile may include an identifier generated and/or assigned by the HES to identify this message as a unique transaction, such as a transaction identifier.

In one aspect, the profiles allow the HES to provide a "post office" assignment between end points using the HES system. The profiles of the HES act as an equivalent zip code or mail stop for each application and location of care (e.g., entity). Once the location of care and application has a "zip code," this is the reference point for HES data mapping and conversion rules between locations of care, applications and message types. Any of these profiles may have or more rules or policies attached or associated with the profile. A message profile may have one or more rules. An entity profile may have one or more rules. An application profile may have one or more rules.

The HES may include a rules engine 196 to apply any one or more rules to the operations and functionality of the HES. Based on any message profile, application profile and/or entity profile, the rules engine may apply one or more rules to any transformation, conversion and/or transmission of data, information and messages between entities using the HES. The rules engine may include any type and form of executable instructions executable or executing on any device. The rules engine may read and understand rules in any predetermined format. The rules or rules engine may be configured by a user of the HES. The rules may be specified by an entity. The rules may direct, instruct or control the way the HES converts, transforms and/or transmits data, information and messages. The rules may provide conditions upon which an action may be taken. The rules may provide conditions to determine not to take an action. The rules may include any type and form of logical constructs and/or expressions.

The HES may include a transformation engine 198 to provide transformation of any data, information or message from one type or format to another type or format. The transformation engine may include any type and form of executable instructions executable or executing on any device. The transformation engine may be responsive to any profile 194 and/or the rules engine 196. In some embodiments, the transformation engine transforms unstructured data into structured data. In some embodiments, the transformation engine transforms a document of one format into a document of another format. In some embodiments, the transformation engine transforms data of one application into data processable by another application.

Figure 1C:
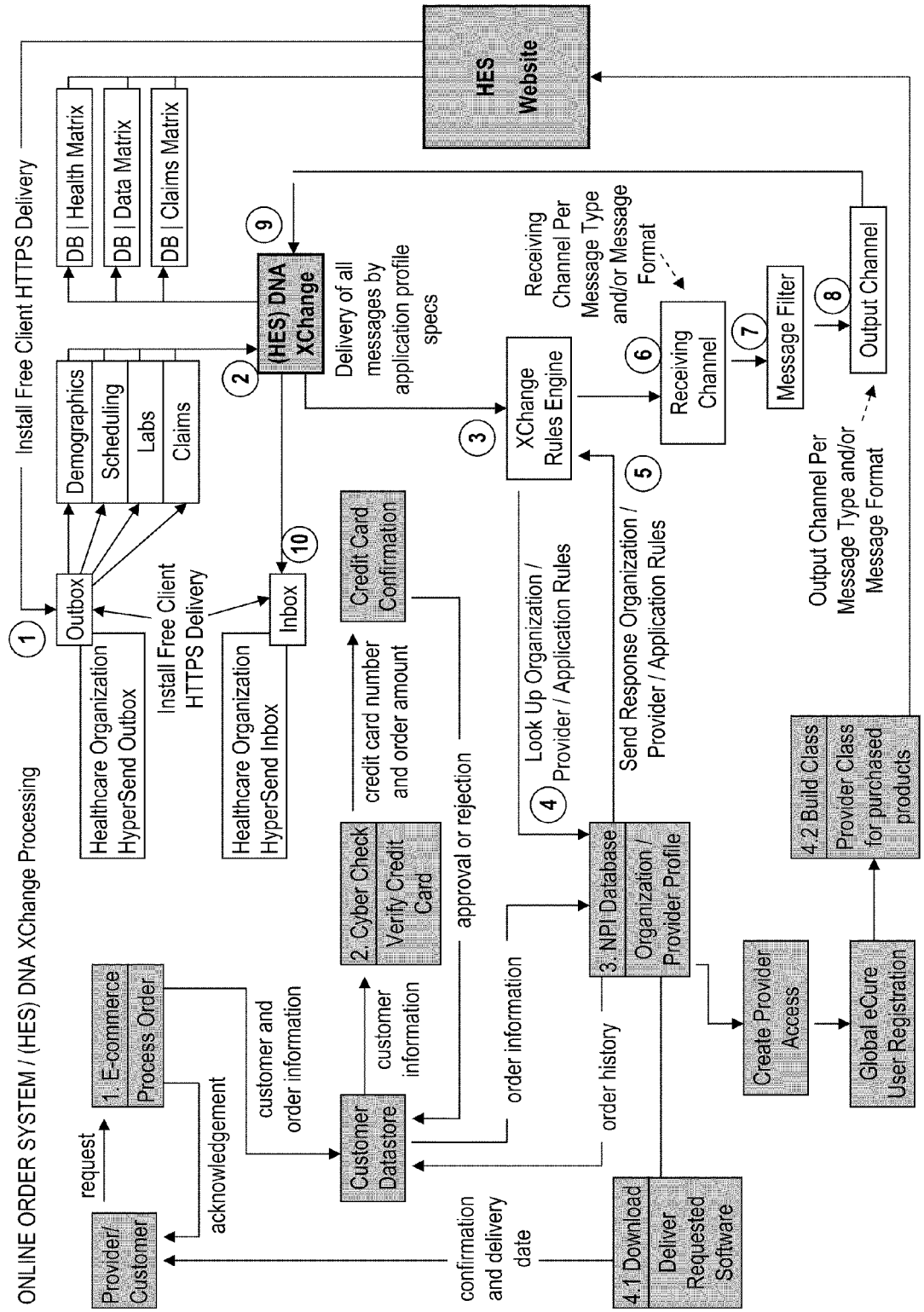
FIG. 1C is a block diagram of another embodiment of an environment for a healthcare exchange system.
Figure 1D:
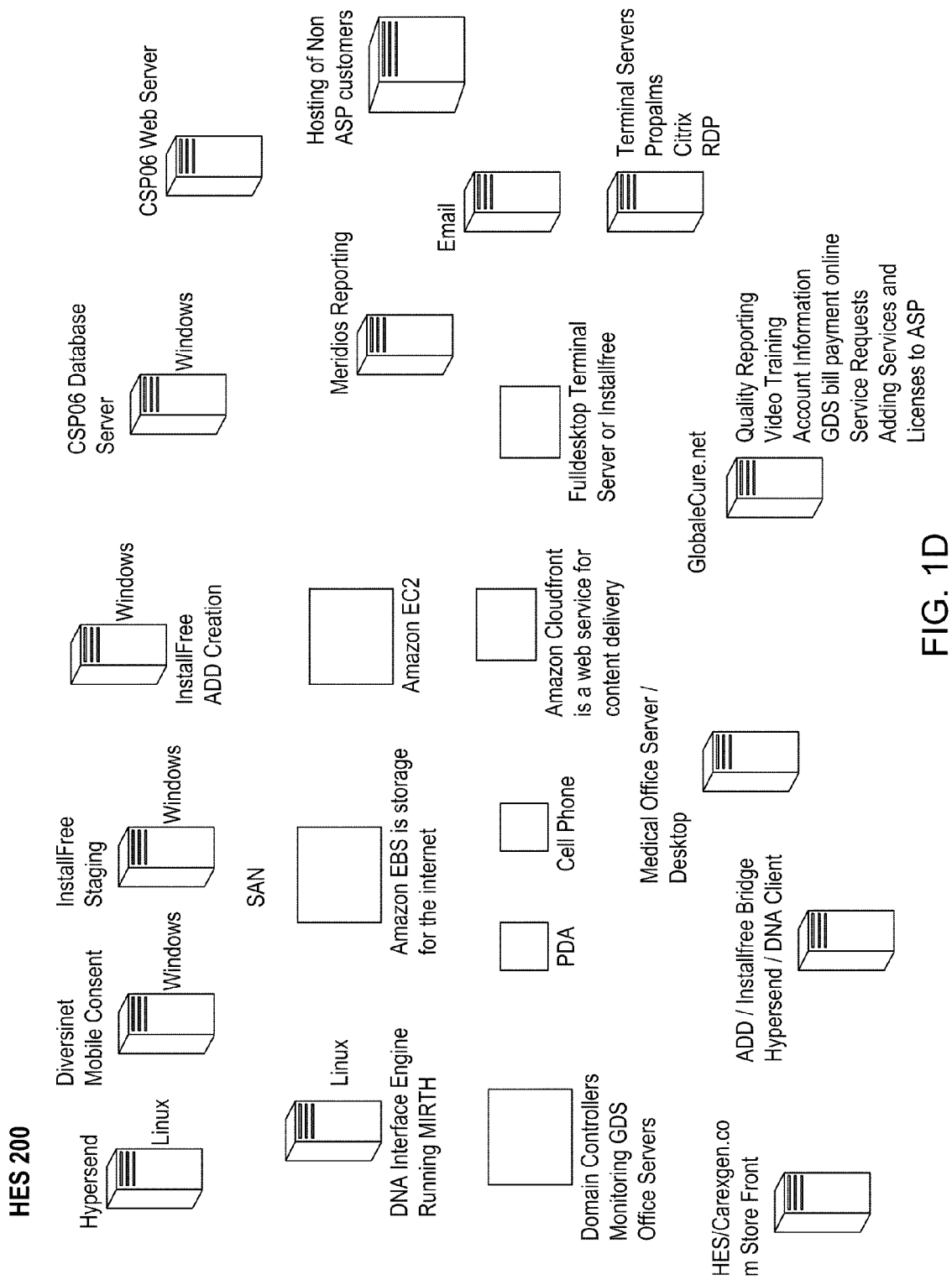
FIG. 1D is a block diagram of another embodiment of an environment for a healthcare exchange system.

Referring now to FIGS. 1C and 1D, example embodiments of an HES system are depicted. FIG. 1C illustrates an embodiment of an HES system, such as using an Online Order System. The HES may also be referred to as a DNA exchange system or DNA XChange system. FIG. 1C illustrates a provider or a customer sending a request to an E-commerce component of the HES system. The request may be a request for a process order or any other type of client or service request. The E-commerce may send an acknowledgment reply back to the provider or customer. The E-commerce may further send to a storage, such as a Customer Datastore, the customer and order information. Customer Datastore may store the customer and order information and send the customer information to another component of the system, such as a Cyber Check. The Cyber Check may include a functionality to verify or trigger the verification of the credit card of the customer. The Cyber Check may send the credit card number and order amount relating to the user to another component of the system, such as a Credit Card Confirmation. The Credit Card Confirmation may respond back to the Customer Database with an approval or a rejection of the credit card request and/or order request. The Customer Datastore may send the order information of the customer to a NPI Database which may include an Organization and/or Provider Profile. The NPI database may respond to the Customer Database with an order history relating to the customer. The NPI Database may be in communication with a Download component of the system which may deliver requested software should it be necessary. The NPI Database may also send a request, an instruction or a message to a component, such as Create Provider Access in order to create the access for the provider necessary for the customer request. Create provider Access may be in communication with a HES User Registration in order to register the user. HES User Registration may be in communication with a component, such as Build Class, which may be a provider class for the purchased products.

HES system or DNA XChange System of FIG. 1C may further include install-free client HTTPS delivery. Such Install-free client HTTPS delivery may enable a specific safe and confidential delivery system, protocol or functionality for sending communications between various system components. A Healthcare Organization HyperSend Outbox may be in communication with an Outbox and a Healthcare Organization HyperSend Inbox may be in a communication with an Inbox. Install-free Client HTTPS deliver may be enabled with, operating with or functionalized with both of the Inbox and the Outbox. At step 1, install-free Client HTTPS Delivery may enable and/or provide communication protocols and/or functionality for implementing the HES system features and functions. At step 2, Outbox may be in communication with Demographics, Scheduling, Labs and Claims features and/or components of the HES system. Demographics, Scheduling, Labs and Claims may each be connected with (HES) DNA XChange. HES or DNA XChange may send information to DB Health Matrix, DB Data Matrix and DB Claims Matrix. (HES) DNA XChange may deliver all messages by application profile specifications. At step 3, (HES) DNA XChange may be in communication with XChange Rules Engine. At step 4, XChange Rules Engine may request to look up organization, provider and/or application rules from NPI Database. At step 5, NPI Database may send a response regarding the organization, provider and/or application rules back to XChange Rules Engine. At step 6, Receiving Channel may receive a communication from XChange Rules Engine. Receiving Channel may receive the communication that includes information based on the message type and/or message format. At step 7, Message Filter may receive a communication from the Receiving Channel. Message Filter may filter or process the communication from the Receiving Channel, based on any set of rules. At step 8, Output Channel may receive a communication from the Message Filter, which may be based on the message type and/or message format. At step 9, Output Channel may send a communication to (HES) DNA XChange. At step 10, (HES) DNA XChange may send a communication to the Inbox. HES Website may be in communication with each of the Outbox, DB Health Matrix, DB Data Matrix and DB Claims Matrix, as well as with the Build Class.

Referring now to FIG. 1D, an embodiment of a HES system is presented, such as a HES ASP DNA Design system. FIG. 1D illustrates various communication and computing devices 100 which could make up or perform any functionality of the HES System described herein. FIG. 1D illustrates a Hypersend operating on a Linux operating system, as well as a Diversinet Mobile Consent on a Windows operating system. Install-free staging may operate on a Windows machine. Install-free ADD Creation may also operate on a Windows machine, as well as CSP06 Database server. HES System may include a CSP06 Web Server, Meridious Reporting, Hosting of non ASP customers, email or email service and terminal servers, propalms, Citrix machines and/or RDP machines or devices. HES system may include fulldesktop Terminal server or Install-free, Amazon cloudfront, Amazon EC2, SAN, Amazon EBS comprising storage for internet, and/or a DNA interface engine running MIRTH, which may operate on a Linux machine. HES System may include domain controllers monitoring GDS office servers, PDAs and cell phones. HES system may include globalecure.com store front, ADD/install-free bridge Hypersend/DNA client, and a medical office server or desktop. An HES web site, such as carexgen.com, may further include quality reporting, video training, account information, GDS bill payment online, service requests, adding services and licenses to ASP, each of which may operate on any machine, device or component described herein.

Embodiments of the present solution implements and represents a universal cloud-based healthcare information exchange that implements Organization, Provider and Application Profiles. The Dynamic Name Attributes ("DNA") or HES solution herein solve global, industry wide healthcare patient portability and interoperability problems.

In an example embodiment, an Application Profile contains any of the following:
  Standard format of data exchange protocols
  HL7 Versions and specs accepted
  XML Standards
  Custom Format
  National Clinical Data Backbone Used
  LOINC (Logical Observation Identifiers Names and Codes
  SNOMED
  Custom Codes
  Certified System ID In an example embodiment, the Organization Profile/Providers Profile (e.g., entity profiles) contains and of the following:
  Certified System ID
  Healthcare Organization Tax ID
  NPI's of all Provider within the Healthcare Organization Healthcare Organization Tax ID
Healthcare Organization Name
Healthcare Organization Full Address
Healthcare Organization Phone Number
Healthcare Organization Fax Number
Healthcare Organization Email
Providers Full Name
Providers DOB
Providers Email Address
Providers Phone Number
Providers DEA In some embodiments, secure delivery of patient information is provided via any type and form of secure communications interface. In some embodiments, Secure Socket Layers (SSL) or Transport Layer Security (TLS) protocols and implementation is used for secure delivery or exchange between entities via the HES. For example, in one embodiment, HyperSend, an OEM Peer to Peer Secure Delivery may be used by the HES system. The secure delivery mechanism may work with any type and of electronic file, including Word, Excel, CSV, HL7 CCD, EDI, PACS Images.

The HES may include any type and form of interface engine to support the communication formats of disparate medical hardware, software and payors. For example, in one embodiments, the interface engine may be use or incorporate a MIRTH open source interface engine, which allows for the sending and receiving of TCP/IP Socket communication or file based sending and receiving. In some embodiments, attaching or interfacing the interface engine to a data source allows for the storing of the sending and receiving transactions and files. The HES may parse or dissect the incoming messages and build any type of export format required or requested by the receiving system. The HES may read the message headers and formats to create a message profile. Creating the message profile allows HES to provide a post office assignment of a zip code to each application and location of care. The message header may include the following elements:

Sending Location (e.g. Labs);
Receiving Location (e.g. PMA);
Message Type (e.g. ORU, MDM);
Format Version of Sending Application (e.g. HL7 2.3); and
ACK Message Requirements for sending systems.

Once the location of care and application has a zip code via a message profile, this is the reference point for all of the data mapping and conversion rules engine between locations of care, applications and message types.

The rules engine may inspect the content of the message to apply managed care models, LOINC, SNOMED and discrete data element requirements. The rule engine may apply these models and rules in real time. At this point, in some embodiments, the HES performs mapping for any data elements to create the conversion based on zip code of application to application rules.

Once the application to application mapping has been performed, the HES may pass the mapped message to apply location of care export rules based on the content that zip code wants to receive. The HES may create the following:

Location of care profile and routing number
Application sub profile and sub routing number
Message type sub profile and sub routing number
Mapping necessary to apply to destination
DNA tagging of all Patient's or EMPI (Electronic Master Patient Index) logic
Ready to Export and securely deliver the results to the destination system.

In some embodiments, InstallFree encapsulation is applied to DNA client or interface and National Provider Index numbers as the email address to one domain name, such as a domain name of the HES, for example CareXgen.com. Pre registering every doctor in the United States would enable each to receive the electronic medical results securely and free.

Implementation of the system and as illustrated in the block diagrams starts with, in some embodiments, registration of patients in all healthcare systems under the same Tax ID. The following is example embodiment of a database format:

<System Name> Define How you are going to track which system registered the Patient
<Patient First Name>
<Patient Middle Name>
<Patient Last Name>
<Patient DOB>
<Patient City>
<Patient State>
<Patient Zip Code>
<Patient Country>
<System ID> Created by auto generation upon new system name
<System Patient ID> Bring forward the System patient ID that the registration system
<Healthcare Organization Patient ID> This groups all registered patient that have a match from all System ID's.

Once this patient registration format is defined the HES exists to create a patient exchange or post office for patient records. The HES may be a bidirectional solution that does not revolve around retraining all the registration staff to learn new master patient index software.

In some embodiments, The system further implements automated extraction of the data fields and format above from any software in the healthcare organization. Any software that stores patient information has some kind of database. Exporting the patient data can be easier than importing the patient data into all these systems. Most healthcare information software currently offers an import and export feature with a universal format like HL7/XML.

In some aspects, the HES implements various technologies together to maintain the ease of use and lower cost. In one embodiment, a Registration Application running on a workstation or a server sends demographics message in the national standard format of fields (example HL7) to the healthcare organization internal database/repository for tracking and processing. This database can be either hosted internally or in a cloud. In some embodiment where the server is hosted in the cloud, the demographics message may be sent via a secure interface.

In some aspects, the HES solution may have distinct areas of opportunities: For example, the HES may used to address the following areas"
1. one to one entity communications
2. Electronic medical records to other electronic medical records applications or practice management systems
3. Electronic medical records to hospitals
4. Electronic medical records to HL7 devices
5. Electronic medical records to Labs (Quest, Lab Corp., etc.), Radiology Centers, Community based labs (smaller local labs).

In an embodiment of this model, the HES is connected to as many entities as identified above. This solution may use HyperSend as an interface to or with the HES. For example, HyperSend is used to easily exchange files with customers &

Labs without file size limits of email, or the complexity of FTP. The HyperSend deliveries are secured with the same level of security that protects Internet financial transactions.

Through the (HES) or DNA system or functionality, various organizations may be compatible with and open to servicing a much larger audience of possible new customers.

In embodiments, this model a basic problem of secure delivery of Patient Information may be resolved by utilizing HyperSend—OEM Peer to Peer Secure Delivery embedded into the DNA delivery system. This solution may include Word, Excel, CSV, HL7 CCD, EDI, PACS Images or any type of electronic file.

2. This model, in some embodiments, may be called Message Modification because the DNA may 'convert' various nonstructured data 'documents' (such as for example, Patient Records) and convert them to structured data (such as, for example HL7 ORU).
 a. DNA may take any non-structured patient record (MS Word, Fax, PDF, etc.) and convert it to an HL7 ORU message that is mapped and coded in LOINC.
  i. In the HL7 Standard, an Observation Result (ORU) may be in response to an order and provides clinical observations.
  ii. In HL7 messaging, ORU messages may provide structured patient oriented clinical data between systems (e.g., EKG results to a physician's office). ORU messages may also used for linking orders and results to clinical trials (e.g., new drugs or new devices).
  iii. Clinical observations may include:
 Clinical laboratory results
 Imaging studies (i.e., text)
 EKG pulmonary function studies
 Interpretation
 b. In some embodiments, the purpose of LOINC® is to facilitate the exchange and pooling of clinical results for clinical care, outcomes management, and research by providing a set of universal codes and names to identify laboratory and other clinical observations. The Regenstrief Institute, Inc., an internationally renowned healthcare and informatics research organization, may maintain the LOINC database and supporting documentation, and the RELMA (Regenstrief LOINC Mapping Assistant—See, http:loinc.org/relma) mapping program.
 c. In some embodiments, targets for this service may be organizations that need a 'standards based' (LOINC) reporting system to provide Quality Measure Reports, which may be needed to receive more funds/reimbursements from insurance companies, stimulus, and preventable care for patients.
 d. In some embodiments, Meridios may be used as well. The Meridios product healthMATRIX™ 2.0 is a web based health registry application enabling providers, administrators, and staff the ability to manage healthcare data.

3. In some embodiments, A further objective of this system may be to DNA an opportunity to become the standard for universal healthcare data sharing and not require a health data exchange (RHIO's) as other organizations are advocating today. HES or DNA system may be, in some embodiments, based on Napster or iTunes in which a PeerToPeer (PTP) network is created that allows for data sharing but does not require conversion of EMR's, or even for an organization to have an EMR to participate. However, this network would provide solutions to medical related information.

For example, if every doctor had a secure email (outbox) that could transmit patient data (record) securely to a mapping system (DNA) it could then be passed to any other connected system on the PTP network. One of the goals of the present system, in some embodiments, is to get the DNA client into as many providers as possible in as low cost a manner as possible to get them to use the HES as a 'healthcare superhighway'.

In operation, the HES, by creating the message profile, allows the HES to become a post office assigning a zip code, or a zip code like information, to each application and location of care. The message header may include the following 5 elements
 Sending Location (Labs)
 Receiving Location (Practice)
 Message Type (ORU, MDM)
 Format Version of Sending Application (HL7 2.3)
 ACK Message Requirements for sending systems Once the location of care and application has a zip code, or a zip code like information, this information may be used by the HES as a reference point for data mapping and conversion rules engine between locations of care, applications and message types. In some embodiments, the rules engine, may inspect the content of the message to apply real time managed care models, LOINC, SNOMED discrete data element requirements. The HES map perform mapping for any elements to create the conversion based on zip code of application to application rules.

Further to operation in some embodiments, once the application to application mapping has been performed, the HES may pass the mapped message to apply location of care export rules based on the content that zip code wants to receive. The message may create and/or include the following:
 Location of care profile and routing number
 Application sub profile and sub routing number
 Message type sub profile and sub routing number
 Mapping necessary to apply to its destination
 DNA tagging of all Patient's or EMPI logic
 Ready to Export and securely deliver the result to the destination system.

In one embodiment, the system applies the InstallFree encapsulation to DNA client and uses National Provider Index numbers as the email address to one domain name, for example, CareXgen.com. Pre registering every doctor in the United States to receive the electronic medical results securely facilitates a "universal" cloud based mechanism.

In some embodiments, the HES manages secure TCP/IP and File based inbound and out bound communication channels for patient data in markup formats. Formats may include:
 HL7 (Any Version)
 DICOM
 XML
 CSV
 XLS
 EDI
 ELINCS
 CCD
 CCR
 CDA
 ASTM
 MML In some embodiments, the interface engine, rules engine or the HES may include a message filter. The message filter may read segments of an inbound message or read only the segments defined by the rules engine. An example of a filter and/or rules is provided below:

```
MSH|^~\&|LabQuest|Practice Name|||19981103000000||ORU|1|P|2.2|||NE||
```

*The Filter is looking for who sent the message and who is receiving the message*

```
PID|1||MR376596||Cramer^Bonnie^||19140408|F|||^^^^||||||189376596 PV1|1|R|E IM||||34
OBR|1|||ML09URIN^Urinalysis||19981103000000|19981103000000||||||||93992^
||||||19981103000000|||F OBX|1|ST|PROTEIN, URN^PROTEIN, URN^L||neg||||||F
OBX|1|ST|GLUCOSE, URN^GLUCOSE, URN^L||neg||||||F OBX|1|ST|BILIRUBIN
UR^BILIRUBINUR^L||neg||||||F OBX|1|ST|KETONES URN^KETONES URN
^L||neg|MG/DL|||||F
OBX|1|ST|PH URINE^PH URINE^L||6.44||||||F OBX|1|ST|SPEC GR URIN^SPEC GR
URIN^L||1.017||||||F OBX|1|ST|WBC DIPSTK U^WBC DIPSTK U^L||neg||||||F
OBX|1|ST|APPEARANCE U^APPEARANCE U^L||Normal||||||F OBX|1|ST|BACTERIA
URN^BACTERIA URN^L||1+||||||F
```

The rules engine or interface engine may parse the message using a parser which may be operating on a hardware of a device. The parser may parse the messages into a data source maintaining file headers and converting data to tables and fields.

Rules may take the information gathered by the Message Filter and then may relay, convert, map or create an entirely new message, such as a HL7 message, based on the criteria given to the Rules that are applied to the outbound channel.

The HES may use Secure Socket Layer communication to transfer files to the cloud, which may be a lower overall cost and maintenance solution. This solution may provide a more secure user friendly connection.

Secure Sockets Layer (SSL), are cryptographic protocols that provide security and data integrity for communications over networks such as the Internet. In one embodiment, this interface 180 is implemented with Hypersend. HyperSend may be an easy to use web based service that bypasses the vulnerabilities of email to deliver important messages, documents or files of any size reliably and securely. The interface, in some embodiments, may exchange important correspondence with anyone in the world quickly and conveniently using just a web browser, through secure data channels that ensure the privacy and authenticity of communications.

In another embodiment, the HES may use or implement Covisint has leveraged its knowledge of enterprise security needs, together with industry standard security technology, to create an entirely web-based solution that enables businesses and individuals to exchange information safely and securely through the Internet, beyond the safe bastions of firewalls and corporate networks.

In some embodiments, the interface and/or interface engine, such as HyperSendm may send deliveries through a secure, encrypted data channel. In some embodiments, HyperSend may be as easy to use as email, yet it may be fundamentally more secure. In some embodiments, HyperSend may achieve secure, reliable, fast, and trackable delivery by relying on the secure data transfer protocols used by web browsers (HTTPS and SSL). Unlike email, which comes to rest on mail server after mail server as it makes it way through the Internet, every HyperSend delivery may be sent as a secure, encrypted stream of data directly to the HyperSend servers. In some embodiments, copies of correspondence may never exist on mail servers, nor may they remain on the HyperSend servers after delivery.

For each send, receive or track deliveries, the HES, such as via interface engine, may establish a user authenticated and encrypted connection between the entity device and the Interface servers, using the same robust security measures used to protect financial transactions on the Internet: industry standard SSL (Secure Sockets Layer) protocol. For authentication and encryption, for example, the HyperSend servers may use a VeriSign Global Site certificate. VeriSign Global Site certificates support 128 bit SSL. HyperSend may achieve a more secure connections for users with browsers that support 128 bit encryption, and also may support secure connections with browsers that support only 40 bit encryption.

In some embodiments, HyperSend may rely on passwords for user authentication. To guard against password theft or interception, HyperSend may use respected methodologies for the secure storage and exchange of passwords. In some embodiments, even HyperSend server administrators do not know a user's password, because passwords are stored in an unreadable form (a one way hash using the MD5 hash algorithm). During log in, the password may be sent through an encrypted connection. The HyperSend servers process the received password (using the MD5 hash algorithm and an arbitrary salt value) and compare the result with the stored form. Only if the two match, is a user admitted.

For additional security in some embodiments, a user may enclose deliveries in an Encrypted Envelope that only the recipient can open. Encrypted Envelopes may use the widely respected Blowfish encryption algorithm, already proven in more than 130 security products. A user may be prompted for a secret word or phrase used to encrypt the delivery on the PC before it is transmitted to the server. The delivery remains encrypted on the HyperSend servers. When the delivery arrives at the recipient's PC, the recipient may enter the same secret word or phrase to open and decrypt the delivery.

The HyperSend web servers, located in data centers of a top tier Internet provider, may be protected around the clock by armed guards, and employ state of the art security procedures to guard against electronic intrusion. The data centers may be located in close proximity to the Internet backbone and staffed 24 hours a day, 7 days a week to ensure prompt delivery of your critical business information.

In some embodiments, it may be important, useful or desired to decide who gets access to this Cloud based healthcare data exchange. In some embodiments, only providers with a National Provider Index number (NPI #) can register for a Cloud Based healthcare data Exchange Client. This may be also how each Provider is allowed to bill for patient care in the United States. This may allow for a log based checks and balances of patient information submitted to the healthcare data exchange against a connection to the insurance companies claims.

With virtually every medical service provider and insurance company in the United States connected together to a Secure Data Exchange Network, without VPNs or Installation of any software attached to the Amazon Cloud. In such configuration, any provider using a practice management system, electronic medical record system or web browser may send a patient record release request to the patient last provider. This provider that now has a medical record release request may simply select the entire medical record of the patient in question to be submitted through the cloud based healthcare data exchange and sends the medical record like an email.

The cloud-based healthcare data exchange may include implementations as follows. In some embodiments, submitted File Formats may include:

File Format from Requesting Entity to the HES
Patient First Name|Patient Middle Name|Patient Last Name|Patient DOB|Patient City|Patient State|Patient ZIP Code|Patient Country|Requesting Healthcare Organization Tax ID|Requesting NPI|Requesting Providers DOB|Requesting Providers DEA #|Requesting System ID|Releasing NPI|

File Format from HES to Receiving Entity
Patient First Name|Patient Middle Name|Patient Last Name|Patient DOB|Patient City|Patient State|Patient Zip Code|Patient Country|Requesting Healthcare Organization Tax ID|Requesting Healthcare Organization Name|Requesting Healthcare Organization Full Address|Requesting Healthcare Organization Phone Number|Requesting Healthcare Organization Fax Number|Requesting Healthcare Organization Email|Requesting NPI|Requesting Providers Full Name|Requesting Providers DOB|Requesting Providers Email Address|Requesting Providers Phone Number|Requesting Providers DEA #|Requesting Certified System ID|Releasing NPI|Releasing Healthcare Organization Tax ID|Releasing Certified System ID|

In some embodiments, once the electronic medical record systems are certified by CCHIT, HITSP and HHS they may be assigned a Certified System ID. This Certified System ID in the Cloud-Based Healthcare Data Exchange controls the application data exchange profile. In some embodiments, Applications not certified may be disabled from submitting to the CloudBased Healthcare Data Exchange. In some embodiments, this concept may be able to certify every medical software and medical device connected. This may reduce the need for healthcare organizations and providers to become healthcare IT professionals to know if the software they have chosen will fit into the interoperability landscape.

In some embodiments, the application Profile may include the following:
Standard format of data exchange protocols
HL7 Versions and specs accepted
XML Standards
National Clinical Data Backbone Used
oLOINC
SNOMED
Certified System ID
May accept queries from cloud based healthcare data exchange.

In some embodiments, the Healthcare Organization Cloud Based Data Exchange Profile may include the following:
Certified System ID
Healthcare Organization Tax ID
NPI's of all Provider within the Healthcare Organization
Healthcare Organization Tax ID
Healthcare Organization Name
Healthcare Organization Full Address
Healthcare Organization Phone Number
Healthcare Organization Fax Number
Healthcare Organization Email
Providers Full Name
Providers DOB
Providers Email Address
Providers Phone Number
Providers DEA All of the above may be referred to as a Healthcare Organization Cloud based Data Exchange Credentialing.

In view of the foregoing, in an illustrative implementation, five entities may participate in the cloud-based data exchange embodiment of the HES. The following represent illustrative examples only:
1. Medical Record Requesting Provider
  a. Ecure Medical Center
    i. 123 Main Street
    ii. Danvers
    iii. MA
    iv. 01923
    v. Tax ID
  b. GE EMR
    i. Certified System ID
      1. GEEMR0000000001
  c. Larry E. Wilson, MD
    i. 03/10/1962 DOB
    ii. 9784569856 Phone
    iii. 9786549875 FAX
    iv. 000123NPI #
    v. 031564879DEA #
2. Patient
  a. Michelle P. Smyth
    i. 01/05/1980
    ii. Danvers
    iii. MA
    iv. 01923
    v. USA
3. Medical Record Requesting Healthcare Organization
  a. Address
    i. 123 Main Street
    ii. Danvers
    iii. MA
    iv. 01923
  b. Tax ID
4. Medical Record Releasing Healthcare Organization
  a. Name
  b. Address
  c. Tax ID
5. Medical Record Releasing Provider
  a. Global Medical Center
    i. 123 South Street
    ii. Denver
    iii. CO
    iv. 86459
    v. Tax ID
  b. ALLScripts
    i. Certified System ID
      1. AllScripts0000000010
  c. Mark E. Jones, MD
    i. 03/10/1964 DOB
    ii. 4564569856 Phone
    iii. 4566549875 FAX
    iv. 123000NPI #
    v. 123456789DEA #

The foregoing example may include illustrative participants and associated illustrative data that provide an illustrative case to follow a patient through the exchange.

In some embodiments, Amazon Cloud Computing may be users for the Healthcare Data Exchange (DNA). A further feature in an illustrative embodiment is a provision of a Certified System ID's for a vendor registry to have the vendors apply for certified system ID's.

In some embodiments described herein, using SSL leverages the power of the internet in the most secure and cost effective manner available. HyperSend may work like email without the security concerns and user learning curves. InstallFree Application Virtualization Solves Legacy Healthcare Organization problems. The Healthcare Data Exchange may make Provider communication secure and verifiable through checks and balances with the insurance companies.

The data exchange, in some embodiments, may not store the patient information on the internet, but it rather may simply exchange it from peer to peer.

In some embodiments, The InstallFree Bubble may deliver the HyperSend email system without installing it to the workstation, but may use all the power of the workstation. This may be done over the Internet any time the workstation or server that is connected to the Internet is turned on. This may also be done without user intervention or login. InstallFree bubble may be delivered that connects to the data exchange with an NPI # and a certified system ID. This embodiment may be referred to as a "bubble" because it is safe inside the virtualized application. In this case HyperSend may be the bubble and the servers in the sky (Cloud Computing).

In the illustrative embodiment, a Patient medical record request file may be of any size, for example approximately 2 k.

In some embodiments, once the Provider receives the request for medical records, it may release the medical records. Depending on each document type, discrete clinical data backbone and data format within the electronic medical system that is releasing the medical records versus the receiving electronic medical record system, there may be many things to consider.

In some embodiments, each of the electronic medical record systems may have a Certified System ID and have a standard data format, but a nonstandard discrete clinical data backbone.

In some embodiments, a standard format could be implemented, which is a clinical summary of information, referred to illustratively as a Continuity Care Document CCD or Continuity Care Record CCR.

In some embodiments, the conversion of text documents to structured clinical data may be based on the understanding of the provider who has to read and treat patients based on the data converted for that provider.

In some embodiments, there may be 2 steps to converting information to electronic data.

At step 1, in some embodiments, a paper copy of a document in its final signed status that has been faxed, printed or digitally saved and dissect it in this manner below may be acquired. This may be the process of creating a Certified System ID based document type profile with provider workflow.

Originating System: AllScripts Touch Works
Document Type: Internal Correspondence
Document Type Abbreviation: IC
Document Format Type: Text Only
Document Content: Free text Zero Structure In some embodiments, the "provider" may be placed in a Responsible Provider discrete data field in both the HES and the Clinical Data Point in Providers EMR

| MAP Description/Document Profile | Captured Field | HES | Clinical Data Point in provider EMR |
| --- | --- | --- | --- |
| Responsible Provider | provider | respprov | ResponPro |
| Color | yellow | Test Color | tcolor |
| Male | he | SEXM | Sex |
| Female | she | SEXF | Sex |

In some embodiments, once all Text is captured and fields are defined step 2 may be implemented.

In some embodiments, at step 2, joining the application profile, provider profile and document type profile in the formats as described above may be implemented. This may become a unique inbound message profile for all 3 elements.

Application Profile: Allscripts V1|Profile ID 0123456789
Document Type: Internal Correspondence|Profile ID 0123456789^IC
Provider ID: Larry E. Wilson, MD|Profile ID 000123
Unique Inbound ID: 0123456789^IC^000123

In some embodiments, the Unique Inbound ID becomes a saved profile for the provider transmitting documents to the exchange and how they should be handled.

In some embodiments, once all document types from one application have been implemented and a map into the clinical data backbone is created, custom needs may be applied for a certain provider against the master clinical data backbone and the provider's dictation if needed. In some embodiments, the need for text document conversion to structure data entered to the clinical data backbone may be illustratively described.

Figure 1E:
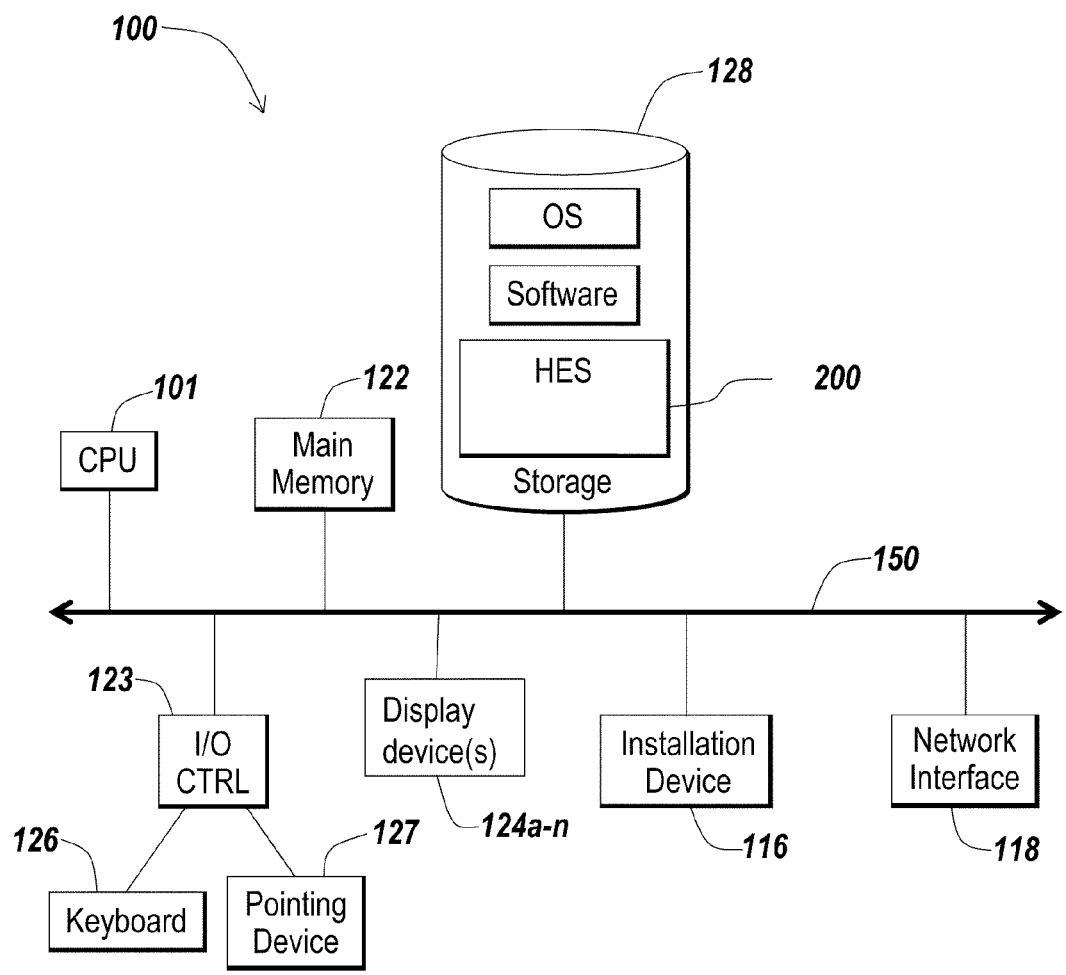
FIGS. 1E-1H are block diagrams of embodiments of a computing device.
Figure 1F:
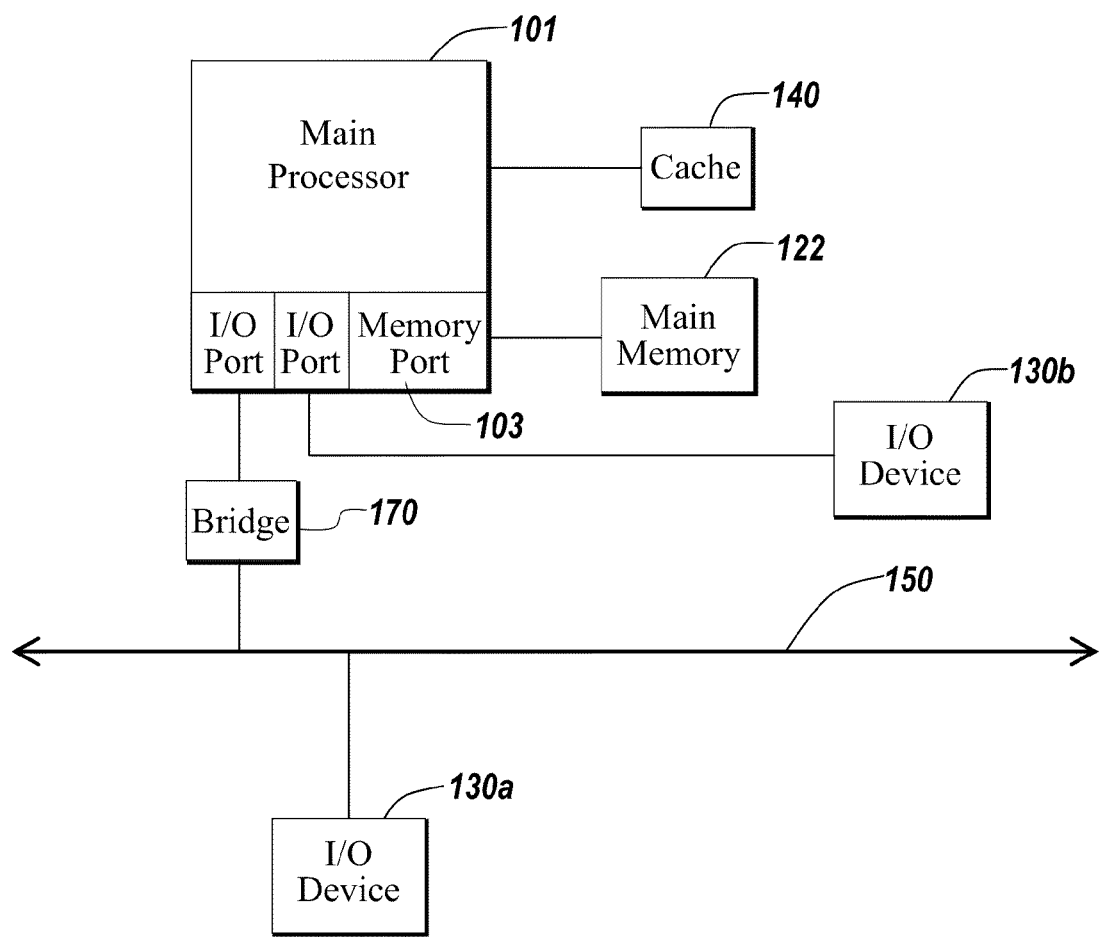

Referring now to FIGS. 1E and 1F, the client 102, server 106, and HES 200 may be deployed as and/or executed on any type and form of computing device, such as a computer, network device or appliance capable of communicating on any type and form of network and performing the operations described herein. FIGS. 1E and 1F depict block diagrams of a computing device 100 useful for practicing an embodiment of the client 102, server 106 or appliance 200. As shown in FIGS. 1E and 1F, each computing device 100 includes a central processing unit 101, and a main memory unit 122. As shown in FIG. 1E, a computing device 100 may include a visual display device 124, a keyboard 126 and/or a pointing device 127, such as a mouse. Each computing device 100 may also include additional optional elements, such as one or more input/output devices 130a-130b (generally referred to using reference numeral 130), and a cache memory 140 in communication with the central processing unit 101.

The central processing unit 101 is any logic circuitry that responds to and processes instructions fetched from the main memory unit 122. In many embodiments, the central processing unit is provided by a microprocessor unit, such as: those manufactured by Intel Corporation of Mountain View, Calif.; those manufactured by Motorola Corporation of Schaumburg, Ill.; those manufactured by Transmeta Corporation of Santa Clara, Calif.; the RS/6000 processor, those manufactured by International Business Machines of White Plains, N.Y.; or those manufactured by Advanced Micro Devices of Sunnyvale, Calif. The computing device 100 may be based on any of these processors, or any other processor capable of operating as described herein.

Main memory unit 122 may be one or more memory chips capable of storing data and allowing any storage location to be directly accessed by the microprocessor 101, such as Static random access memory (SRAM), Burst SRAM or Synch-Burst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDEC SRAM, PC100 SDRAM, Double Data Rate SDRAM (DDR SDRAM), Enhanced SDRAM (ESDRAM), SyncLink DRAM (SLDRAM), Direct Rambus DRAM (DRDRAM), or Ferroelectric RAM (FRAM). The main memory 122 may be based on any of the above described memory chips, or any other available memory chips capable of operating as described herein. In the embodiment shown in FIG. 1E, the processor 101 communicates with main memory 122 via a system bus 150 (described in more detail below). FIG. 1F depicts an embodiment of a computing device 100 in which the processor communicates directly with main memory 122 via a memory port 103. For example, in FIG. 1F the main memory 122 may be DRDRAM.

FIG. 1F depicts an embodiment in which the main processor 101 communicates directly with cache memory 140 via a secondary bus, sometimes referred to as a backside bus. In other embodiments, the main processor 101 communicates with cache memory 140 using the system bus 150. Cache memory 140 typically has a faster response time than main memory 122 and is typically provided by SRAM, BSRAM, or EDRAM. In the embodiment shown in FIG. 1F, the processor 101 communicates with various I/O devices 130 via a local system bus 150. Various busses may be used to connect the central processing unit 101 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 101 may use an Advanced Graphics Port (AGP) to communicate with the display 124. FIG. 1F depicts an embodiment of a computer 100 in which the main processor 101 communicates directly with I/O device 130b via HyperTransport, Rapid I/O, or InfiniBand. FIG. 1F also depicts an embodiment in which local busses and direct communication are mixed: the processor 101 communicates with I/O device 130b using a local interconnect bus while communicating with I/O device 130a directly.

The computing device 100 may support any suitable installation device 116, such as a floppy disk drive for receiving floppy disks such as 3.5-inch, 5.25-inch disks or ZIP disks, a CD-ROM drive, a CD-R/RW drive, a DVD-ROM drive, tape drives of various formats, USB device, hard-drive or any other device suitable for installing software and programs such as any for HES 200, or portion thereof. The computing device 100 may further comprise a storage device 128, such as one or more hard disk drives or redundant arrays of independent disks, for storing an operating system and other related software, and for storing application software programs such as any program related to the HES 200. Optionally, any of the installation devices 116 could also be used as the storage device 128. Additionally, the operating system and the software can be run from a bootable medium, for example, a bootable CD, such as KNOPPIX®, a bootable CD for GNU/Linux that is available as a GNU/Linux distribution from knoppix.net.

Furthermore, the computing device 100 may include a network interface 118 to interface to a Local Area Network (LAN), Wide Area Network (WAN) or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, or some combination of any or all of the above. The network interface 118 may comprise a built-in network adapter, network interface card, PCMCIA network card, card bus network adapter, wireless network adapter, USB network adapter, modem or any other device suitable for interfacing the computing device 100 to any type of network capable of communication and performing the operations described herein.

A wide variety of I/O devices 130a-130n may be present in the computing device 100. Input devices include keyboards, mice, trackpads, trackballs, microphones, and drawing tablets. Output devices include video displays, speakers, inkjet printers, laser printers, and dye-sublimation printers. The I/O devices 130 may be controlled by an I/O controller 123 as shown in FIG. 1E. The I/O controller may control one or more I/O devices such as a keyboard 126 and a pointing device 127, e.g., a mouse or optical pen. Furthermore, an I/O device may also provide storage 128 and/or an installation medium 116 for the computing device 100. In still other embodiments, the computing device 100 may provide USB connections to receive handheld USB storage devices such as the USB Flash Drive line of devices manufactured by Twintech Industry, Inc. of Los Alamitos, Calif.

In some embodiments, the computing device 100 may comprise or be connected to multiple display devices 124a-124n, which each may be of the same or different type and/or form. As such, any of the I/O devices 130a-130n and/or the I/O controller 123 may comprise any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may comprise multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices, such as computing devices 100a and 100b connected to the computing device 100, for example, via a network. These embodiments may include any type of software designed and constructed to use another computer's display device as a second display device 124a for the computing device 100. One ordinarily skilled in the art will recognize and appreciate the various ways and embodiments that a computing device 100 may be configured to have multiple display devices 124a-124n.

In further embodiments, an I/O device 130 may be a bridge 170 between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus.

A computing device 100 of the sort depicted in FIGS. 1E and 1F typically operate under the control of operating systems, which control scheduling of tasks and access to system resources. The computing device 100 can be running any operating system such as any of the versions of the Microsoft® Windows operating systems, the different releases of the Unix and Linux operating systems, any version of the Mac OS® for Macintosh computers, any embedded operating system, any real-time operating system, any open source operating system, any proprietary operating system, any operating systems for mobile computing devices, or any other operating system capable of running on the computing device and performing the operations described herein. Typical operating systems include: WINDOWS 3.x, WINDOWS 95, WINDOWS 98, WINDOWS 2000, WINDOWS NT 3.51, WINDOWS NT 4.0, WINDOWS CE, and WINDOWS XP, all of which are manufactured by Microsoft Corporation of Redmond, Wash.; MacOS, manufactured by Apple Computer of Cupertino, Calif.; OS/2, manufactured by International Business Machines of Armonk, N.Y.; and Linux, a freely-available operating system distributed by Caldera Corp. of Salt Lake City, Utah, or any type and/or form of a Unix operating system, among others.

In other embodiments, the computing device 100 may have different processors, operating systems, and input devices consistent with the device. For example, in one embodiment the computer 100 is a Treo 180, 270, 1060, 600 or 650 smart phone manufactured by Palm, Inc. In this embodiment, the Treo smart phone is operated under the control of the PalmOS operating system and includes a stylus input device as well as a five-way navigator device. Moreover, the computing device 100 can be any workstation, desktop computer, laptop or notebook computer, server, handheld computer, mobile telephone, any other computer, or other form of computing or telecommunications device that is capable of communication and that has sufficient processor power and memory capacity to perform the operations described herein.

Figure 1G:
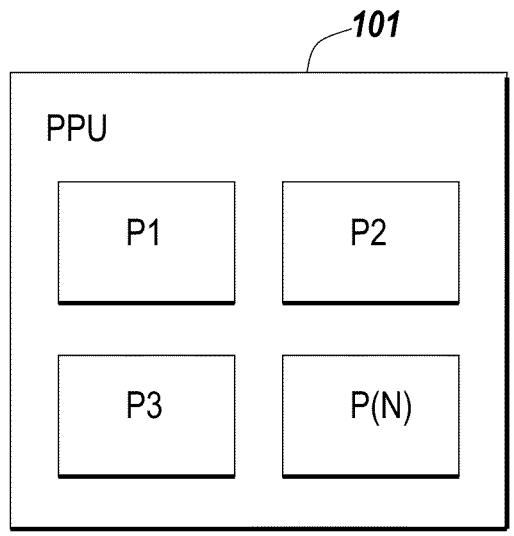

As shown in FIG. 1G, the computing device 100 may comprise multiple processors and may provide functionality for simultaneous execution of instructions or for simultaneous execution of one instruction on more than one piece of data. In some embodiments, the computing device 100 may comprise a parallel processor with one or more cores. In one of these embodiments, the computing device 100 is a shared memory parallel device, with multiple processors and/or multiple processor cores, accessing all available memory as a single global address space. In another of these embodiments, the computing device 100 is a distributed memory parallel device with multiple processors each accessing local memory only. In still another of these embodiments, the computing device 100 has both some memory which is shared and some memory which can only be accessed by particular processors or subsets of processors. In still even another of these embodiments, the computing device 100, such as a multi-core microprocessor, combines two or more independent processors into a single package, often a single integrated circuit (IC). In yet another of these embodiments, the computing device 100 includes a chip having a CELL BROADBAND ENGINE architecture and including a Power processor element and a plurality of synergistic processing elements, the Power processor element and the plurality of synergistic processing elements linked together by an internal high speed bus, which may be referred to as an element interconnect bus.

In some embodiments, the processors provide functionality for execution of a single instruction simultaneously on multiple pieces of data (SIMD). In other embodiments, the processors provide functionality for execution of multiple instructions simultaneously on multiple pieces of data (MIMD). In still other embodiments, the processor may use any combination of SIMD and MIMD cores in a single device.

Figure 1H:
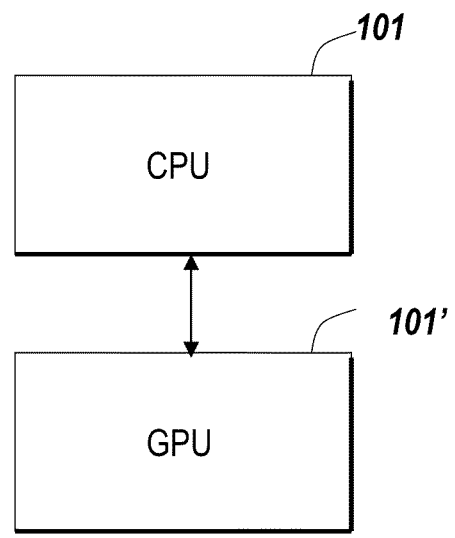

In some embodiments, the computing device 100 may comprise a graphics processing unit. In one of these embodiments, depicted in FIG. 1H, the computing device 100 includes at least one central processing unit 101 and at least one graphics processing unit. In another of these embodiments, the computing device 100 includes at least one parallel processing unit and at least one graphics processing unit. In still another of these embodiments, the computing device 100 includes a plurality of processing units of any type, one of the plurality of processing units comprising a graphics processing unit.

Figure 2:
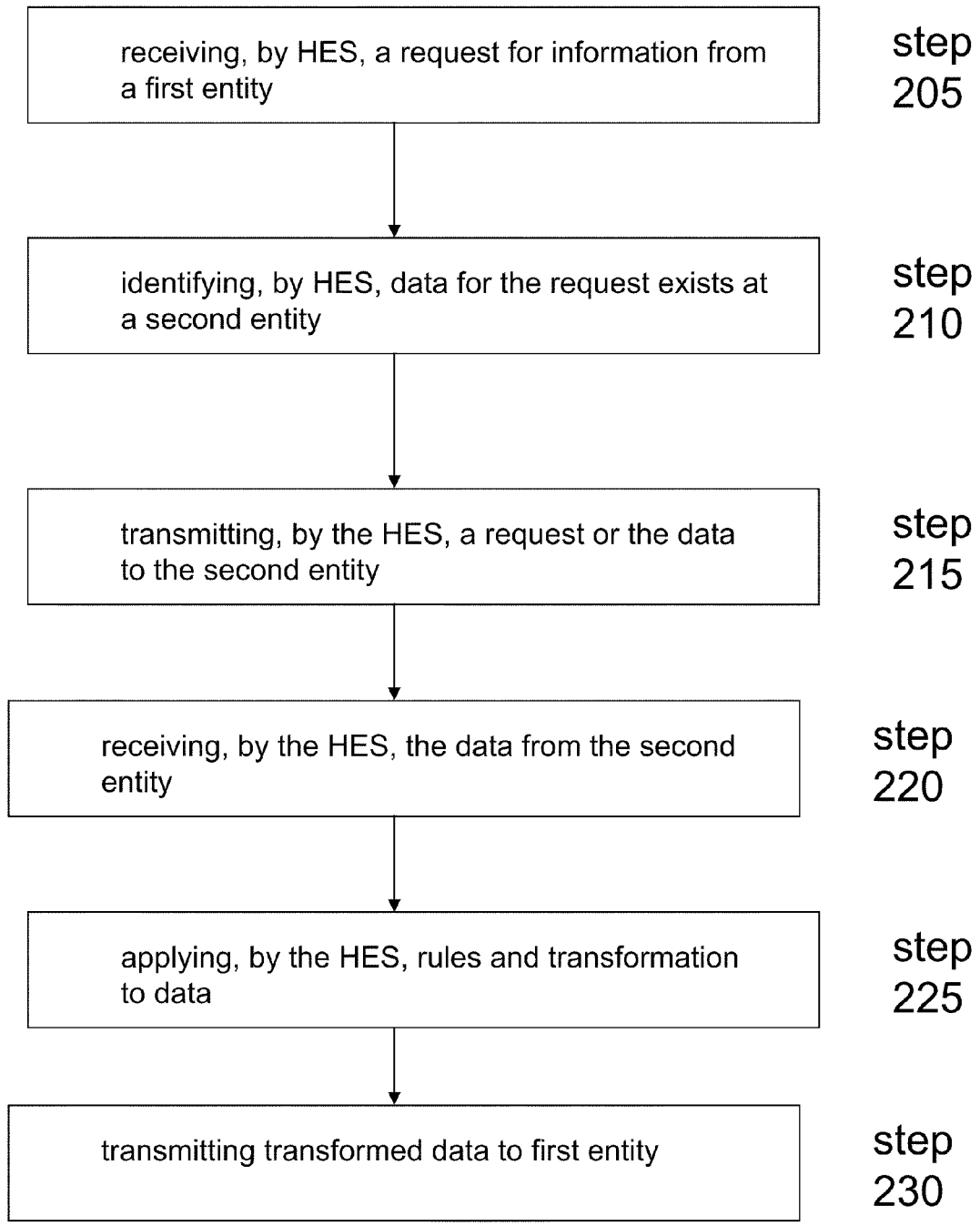
FIG. 2 is a flow diagram of embodiments of a method of using the healthcare exchange system.

Referring now to FIG. 2, embodiments of steps of a method for exchanging data via a healthcare exchange system is depicted. In brief overview, at step 205, a healthcare exchange system receives from an application of a first healthcare entity a request for information of a patient. At step 210, the healthcare exchange system identifies that a second healthcare entity has a record of a plurality of records of the patient. The record is stored by the second healthcare entity in a format identified by a profile of the second healthcare entity. At step 215, the healthcare exchange system transmits a request to the second healthcare entity for release of the patient record. At step 220, the healthcare exchange system receives the record of the patient in the format of an application of the second healthcare entity. At step 225, the healthcare exchange system automatically transforms the patient record to a format identified by a profile of the first healthcare entity. At step 230, the healthcare exchange system transmits the patient record in the transformed format to the first healthcare entity responsive to the request of the first healthcare entity.

At step 205, the healthcare exchange system may receive a request from any type of entity. The request may include a query for information on the patient accessible via the healthcare exchange system. The request may comprise a query for a specific type of record of the patient. The request may comprise a request for a medical record of the patient. The request may comprise a request for a particular type of record, such as a particular medical record. The request may comprise a request for a plurality of records of the patient. The request may comprise a request for any or all records of records known by the HES or otherwise accessible via the HES. The request may comprise any of the element of a message profiles, such as a sending location, receiving location, message type, format and version and acknowledgement requirements.

The healthcare exchange system may receive the request via any type of protocol, such as HTTP. The healthcare exchange system may receive the request via socket based or TCP layer connection. The HES may receive the request by obtaining the request via the outbox of the interface 180. The HES may receive the request by obtaining the request from a folder or storage location on a device of the requesting entity.

At step 210, the healthcare exchange system identifies via HIE records the entities and applications that have records of the patient. The HES may identify a plurality of entities storing records of the patient externally to the HES. The HES may identify another healthcare entity that has a requested record of the patient. The HES may enumerate the healthcare entities that have records of the patient and organize the enumeration by record types and/or entity types and/or application types. The HES may identify which entity has a specific record or type of record. The HES may identify entities having records based on any temporal information. The HES may identify a plurality of entities that have the same record. The HES may identify entities with different applications that have the same record.

The HES may query the HIE records stored in an HIE records database to identify HIE records of the patient. The HES may generate HIE records and populate the HIE database based on processing of data, information and messages exchanged via the HES. For example, the HES may parse any office documents or electronic files to identify patients and patient records from structured and/or unstructured data of the document or file. From the exchange between entities, the HES can identify the source of the record and the application associated with the record. From the HIE records of the patient, the HES can determine the records that have been identified by the HES for the patient and the location of the record, such as by entity and/or application At step 215, the HES may transmit requests to one or more entities for records of the patient. In some embodiments, the HES may transmit a request to release the records of the patient from the entity. The HES may transmit a request to authorize release or transmission of the patient record from the entity. The HES may transmit a request for the entity to send, transmit or provide the record. The HES may send a plurality of a requests to a plurality of entities for records of a patient.

The interface engine of the HES may transmit the request via the interface of the entity, such as putting or sending the request to the entity's inbox. The HES may transmit the request to the application of the second entity. The HES may interface directly with the entity's application. The HES may request the record in one format of a plurality of formats supported by the entity and/or application. The HES may send the request using a protocol and/or interface supported by the entity and/or application. The HES may identify the entity profile of the second entity and the application profile for the application of the second entity to determine the format, protocol and interface to communicate with the second entity. The HES may construct and transmit the request in accordance with any entity, application and/or message profile.

At step 220, the HES may receive the requested record of the patient from one or more entities. The HES may receive the requested record(s) in a format and via a protocol and an interface corresponding to the second entity, the second entity's application and/or second entity's interface. The format of the record and the protocol for receiving the record may be different than that of the first entity. In some embodiments, the HES receives a medical record of the patient or patient record in the format of the application of the second healthcare entity. In some embodiments, the second entity exports the records from the application. The second entity may store the exported record via the interface, such as in the outbox or a folder representing the outbox. In some embodiments, the HES receives the medical record of the patient or patient record via a message type identified by the profile of the second healthcare entity and/or application profile for the application of the second entity.

The HES may receive the record or records of the patient via communications or interface between the interface engine of the HES and the interface 180 of the second entity. In some embodiments, the second entity transmits via an application via the interface the records to the HES. In some embodiments, the HES may obtain or pull the records from the system of the second entity, such as via the interface 180. In some embodiments, the HES may read the outbox of the interface of the second entity to obtain one or more records.

At step 225, the HES may apply any one or more rules to the records received from the second entity. In some embodiments, the HES may apply one or more rules based on the application profile for the application of the second entity. In some embodiments, the HES may apply one or more rules associated with or identified by entity profile of the second entity. In some embodiments, the HES may apply one or more rules associated with or identified by a message profile for the transaction. In some embodiments, the HES may pre-process the record from the second entity prior to transforming to a format and/or protocol for the first entity. In some embodiments, the HES may apply rules for filtering, clean up of data, dealing with unstructured data or addressing particular data and protocols of the second entity or second entity application. In some embodiments, the HES may apply rules to modify, remove or add any one or more data elements to or form the record, In some embodiments, the HES may apply rules to convert the data from one model to another model. In some embodiments, the HES may apply rules to convert the data from one set of codes and/or names to another set of codes/and or names. In some embodiments, the HES may apply rules to map data items from one data, messaging or protocol model to data items corresponding to another data, messaging or protocol model. In some embodiments, the HES may apply rules to convert the record and/or data items therein from one data, messaging or protocol model to another data, messaging or protocol model.

The HES may transform the record of the patient from a format of the application of the second entity to a format for the application of the first entity. The HES may transform the record after applying one or more rules. The HES may transform the record before applying one or more rules. The HES may apply one or more rules, transform the record and then apply one or more rules to the transformed record. For example, the HES may apply one or more export rules to the record from the second entity, transform the record, and apply one or more import rules to the record for the first entity. The HES may transform the record from the second entity in accordance with a format version of the sending application identified in a message profile. The HES may transform the record from the second entity in accordance with a format for an application of the first entity identified via an application profile and/or entity profile.

The HES may apply rules and/or transformation to provide a copy or version of the record from the second entity that is seamlessly and transparently acceptable, suitable or processable by an application of the first entity. The HES may apply rules and/or transformation to provide a copy or version of the record from the second entity that meets the format, protocol and interface of the second entity and the second entity application. The HES applies these rules and/or transformation automatically and configurable and flexible manner based on entity, application and message profiles.

At step 230, the HES communicates or transmits the transformed record of the patient to the first entity or requesting entity. The interface engine of the HES may transmit or communicate the record in a format acceptable by the first entity via the interface of the first entity. In some embodiments, the interface engine communicates the record to the inbox of the first entity. In some embodiments, the interface engine stores the record to a predetermined folder or direct of a device of the first entity. In some embodiments, the interface engine communicates the record to the application of the first entity. In some embodiments, the interface engine communicates the record or stores the record to a records repository of the first entity. The record communicated to the first entity may be in a format and/or protocol identified by the application profile.

The HES may determine the entity to send the record to via the entity profile and/or message profile.

In communications to any entity, the HES may check for and provide any reliability of delivery of transmission of requests and/or records. The HES may perform or check for any confirmation or acknowledgement of receipt of any requests and/or responses. The HES may perform or check for any confirmation or acknowledgement of receipt of transmission of a patient record. The HES may perform reliability of delivery or check for or send acknowledgments of receipt responsive to any application and/or message profile, such as a profile's specification for acknowledgments. The HES may perform reliability of delivery or check for or send acknowledgments of receipt responsive to any protocol of an interface or application. The HES may perform reliability of delivery or check for or send acknowledgments of receipt responsive to any protocol identified via an application and/or message profile.

Although the above method is generally describes as requests and responses between entities and the HES, in some embodiments, entities may communicate with each other via peer-to-peer technology. In some embodiments, the request of the first entity may be communicated to the second entity via the peer-to-peer technology, which may or may not traverse the HES. In some embodiments, the HES facilitates the establishment of communications between entities by providing location of record services and entity, application and messaging profiling. In some embodiments, the HES and/or portions therefore of execute or are distributed to devices of each of the entities for executing any of the operations and functionality described herein.

Although the systems and methods discussed herein are generally described in the healthcare content, the exchange systems and methods may be used in any content or industry and for exchanging data, information and messages between entities in that environment. The exchange system provides an efficient and flexible approach to requesting, locating and exchanging records between disparate and disjoint entities and applications which may use different formats and/or protocols. Instead of creating new silos of databases and centralized copies of records, the exchange system provides an efficient and flexible to leverage existing records repositories and applications while allowing others seamless access to those existing repositories in a secure, easy to use manner.

What is claimed is:

1. A method for exchanging healthcare information via a healthcare exchange system, the method comprising:
    (a) receiving, by a healthcare exchange system in communication with a plurality of health care entities via one or more networks a first request, from a first application executing on a client computing device of a first healthcare entity, for medical information of a patient of a plurality patients;
    (b) identifying, by the healthcare exchange system, that a second healthcare entity has a medical record of a plurality of medical records of the patient, the medical record stored by the second healthcare entity in a second format identified by a second profile of the second healthcare entity, the second profile identifying the second format used by a second application executing on a device of the second healthcare entity;
    (c) transmitting, by the healthcare exchange system via the one or more networks, a second request to the second application of the second healthcare entity to authorize release of the medical record to an entity identifier corresponding to the first healthcare entity;
    (d) receiving, by the healthcare exchange system via the one or more networks, the medical record of the patient in the second format used by the second application responsive to release of the medical record by the second healthcare entity to the entity identifier corresponding to the first healthcare entity;
    (e) automatically transforming, by the healthcare exchange system, the medical record to a first format identified by a first application profile of the first application of the first healthcare entity and using one or more rules of a message profile for the medical record, the first profile identifying the first format used by the first application, the message profile identifying the one or more rules comprising instructions on transforming data of the medical record into the first format of the first application; and
    (f) transmitting, by the healthcare exchange system via the one or more networks, the medical record in the first format to the client computing device of the first healthcare entity responsive to the first request.

2. The method of claim 1, wherein step (a) further comprises receiving, by the healthcare exchange system, the first request comprising a query for information on the patient accessible via the healthcare exchange system.

3. The method of claim 1, wherein step (a) further comprises receiving, by the healthcare exchange system, the first request comprising a query for a specific type of medical record of the patient.

4. The method of claim 1, wherein step (b) further comprises querying, by the healthcare exchange system, patient information stored by the healthcare exchange system, the healthcare exchange system storing portions of patient records transmitted between entities via the healthcare exchange system.

5. The method of claim 1, further comprises storing, by the healthcare exchange system, a healthcare exchange record for the patient that identifies a healthcare entity and an application from which one or more medical records of the patient is stored externally from the healthcare exchange system.

6. The method of claim 1, wherein step (c) further comprises transmitting, by the healthcare exchange system via the one or more networks, the second request to the second healthcare entity via an interface compatible with a second application of the second healthcare entity.

7. The method of claim 1, wherein step (d) further comprises receiving, by the healthcare exchange system via the one or more networks, the medical record of the patient in the second format from a second application of the second healthcare entity.

8. The method of claim 1, wherein step (d) further comprises receiving, by the healthcare exchange system via the one or more networks, the medical record of the patient via a message type identified by the second profile of the second healthcare entity.

9. The method of claim 1, wherein step (e) further comprises identifying the first profile of the first healthcare entity stored in the healthcare exchange system, the first profile identifying the first healthcare entity and format version of a sending application.

10. The method of claim 1, wherein step (f) further comprises transmitting by the healthcare exchange system via the one or more networks, the medical record via a message type identified by the first profile of the first healthcare entity.

11. A system for exchanging healthcare information via a healthcare exchange system, the system comprising:
    a healthcare exchange system operating on one or more servers and in communication with a plurality of health care entities via one or more networks, the healthcare exchange system receiving a first request, from a first application executing on a client computing device of a first healthcare entity, for medical information of a patient of a plurality patients;

a database of the healthcare exchange system identifying that a second healthcare entity has a medical record of a plurality of medical records of the patient, the medical record stored by the second healthcare entity in a second format identified by a second profile of the second healthcare entity, the second profile identifying the second format used by a second application executing on a device of the second healthcare entity;

wherein the healthcare exchange system via the one or more networks, transmits a second request to the second application of the second healthcare entity to authorize release of the medical record to an entity identifier corresponding to the first healthcare entity and receives the medical record of the patient in the second format used by the second application responsive to release of the medical record by the second healthcare entity to the entity identifier corresponding to the first healthcare entity;

an engine of the healthcare exchange system transforming the medical record to a first format identified by a first application profile of the first application of the first healthcare entity and using one or more rules of a message profile for the medical record, the first profile identifying the first format used by the first application, the message profile identifying the one or more rules comprising instructions on transforming data of the medical record into the first format of the first application; and wherein the healthcare exchange system transmits via the one or more networks, the medical record in the first format to the client computing device of the first healthcare entity responsive to the first request.

12. The system of claim 11, wherein the healthcare exchange system receives the first request comprising a query for information on the patient accessible via the healthcare exchange system.

13. The system of claim 11, wherein the healthcare exchange system receives the first request comprising a query for a specific type of medical record of the patient.

14. The system of claim 11, wherein the healthcare exchange system queries patient information stored by the healthcare exchange system, the healthcare exchange system storing portions of patient records transmitted between entities via the healthcare exchange system.

15. The system of claim 11, wherein the database stores a healthcare exchange record for the patient that identifies a healthcare entity and an application from which one or more medical records of the patient is stored externally from the healthcare exchange system.

16. The system of claim 11, wherein the healthcare exchange system transmits via the one or more networks, the second request to the second healthcare entity via an interface compatible with a second application of the second healthcare entity.

17. The system of claim 11, wherein the healthcare exchange system receives via the one or more networks, the medical record of the patient in the second format from a second application of the second healthcare entity.

18. The system of claim 11, wherein the healthcare exchange system receives via the one or more networks, the medical record of the patient via a message type identified by the second profile of the second healthcare entity.

19. The system of claim 11, wherein the healthcare exchange system identifies the first profile of the first healthcare entity stored in the healthcare exchange system, the first profile identifying the first healthcare entity and format version of a sending application.

20. The system of claim 11, wherein the healthcare exchange system transmits via the one or more networks, the medical record via a message type identified by the first profile of the first healthcare entity.

* * * * *